US012094589B2

(12) United States Patent
Tsoukalis

(10) Patent No.: US 12,094,589 B2
(45) Date of Patent: *Sep. 17, 2024

(54) MEDICATION INFUSION SAFETY DEVICE AND A MEDICATION INFUSION DEVICE COMPRISING THE MEDICATION INFUSION SAFETY DEVICE

(71) Applicant: MICREL Medical Devices S.A., Koropi (GR)

(72) Inventor: Achilleas Tsoukalis, Anavyssos Attiki (GR)

(73) Assignee: MICREL Medical Devices S.A., Gerakas (GR)

( * ) Notice: Subject to any disclaimer, the term of this patent is extended or adjusted under 35 U.S.C. 154(b) by 223 days.

This patent is subject to a terminal disclaimer.

(21) Appl. No.: 17/495,331

(22) Filed: Oct. 6, 2021

(65) Prior Publication Data

US 2022/0028516 A1    Jan. 27, 2022

Related U.S. Application Data

(63) Continuation of application No. 14/832,187, filed on Aug. 21, 2015, now Pat. No. 11,302,432.

(30) Foreign Application Priority Data

Aug. 21, 2014 (EP) ..................... 14181804

(51) Int. Cl.
*G16H 20/17* (2018.01)
*A61M 5/142* (2006.01)
*A61M 5/168* (2006.01)
*A61M 5/36* (2006.01)
*G06K 19/077* (2006.01)
*G16H 40/67* (2018.01)

(52) U.S. Cl.
CPC ............ *G16H 20/17* (2018.01); *A61M 5/142* (2013.01); *A61M 5/16813* (2013.01);
(Continued)

(58) Field of Classification Search
CPC ........ A61M 5/142; A61M 2005/14208; A61M 2205/6054; A61M 2205/6072; G06K 19/07758

See application file for complete search history.

(56) References Cited

U.S. PATENT DOCUMENTS 4,925,444 A  *  5/1990  Orkin ................... A61M 39/04
                                                          604/80
5,078,683 A      1/1992  Sancoff et al.
(Continued)

FOREIGN PATENT DOCUMENTS

WO        2008127694 A1    10/2008

OTHER PUBLICATIONS

EP Extended Search Report dated Jan. 26, 2016 from EP Application No. 15181871.3, 10 pages.
(Continued)

*Primary Examiner* — Bradley J Osinski
(74) *Attorney, Agent, or Firm* — Bookoff McAndrews, PLLC

(57) ABSTRACT

A medication infusion device comprises a memory means at a medication reservoir storing data identifying medication in the reservoir, a memory reading means at an infusion pump unit reads data from said memory means, and control means controls an infusion, based on data read by said memory reading means, to start the infusion when the medication is correct. A fluid connection detection means detects fluid connection of the medication reservoir to the infusion pump unit and transmits to control means whether the medication reservoir is connected. The control means controls an infusion in accordance with the transmission from the fluid connection detection means so that when there is no con-
(Continued)

nection between the medication reservoir and infusion pump unit, the infusion pump unit will not be started or, if already started, stopped.

19 Claims, 8 Drawing Sheets

(52) U.S. Cl.
CPC ..... *A61M 5/1689* (2013.01); *G06K 19/07707* (2013.01); *G06K 19/07758* (2013.01); *G16H 40/67* (2018.01); *A61M 2005/14208* (2013.01); *A61M 5/16804* (2013.01); *A61M 5/36* (2013.01); *A61M 2205/6054* (2013.01); *A61M 2205/6072* (2013.01)

(56) References Cited

U.S. PATENT DOCUMENTS

| | | | |
|---|---|---|---|
| 6,685,668 B1* | 2/2004 | Cho | A61M 5/16804 604/118 |
| 7,976,508 B2 | 7/2011 | Hoag | |
| 9,033,939 B2 | 5/2015 | Eberhart et al. | |
| 2002/0038392 A1 | 3/2002 | De La Huerga | |
| 2004/0193453 A1 | 9/2004 | Butterfield et al. | |
| 2006/0206356 A1 | 9/2006 | Vanderveen | |
| 2007/0135765 A1* | 6/2007 | Miller | A61M 5/16827 604/131 |
| 2009/0112178 A1* | 4/2009 | Behzadi | A61M 5/142 604/503 |
| 2011/0152824 A1 | 6/2011 | DiPerna et al. | |
| 2013/0225945 A1 | 8/2013 | Prince et al. | |
| 2014/0066880 A1 | 3/2014 | Prince et al. | |
| 2014/0324019 A1 | 10/2014 | Butterfield et al. | |
| 2015/0001285 A1 | 1/2015 | Halbert et al. | |

OTHER PUBLICATIONS

Extended European Search Report issued on Aug. 11, 2023 in counterpart European Patent Application No. 23168211.3 (11 pages, in English).

* cited by examiner

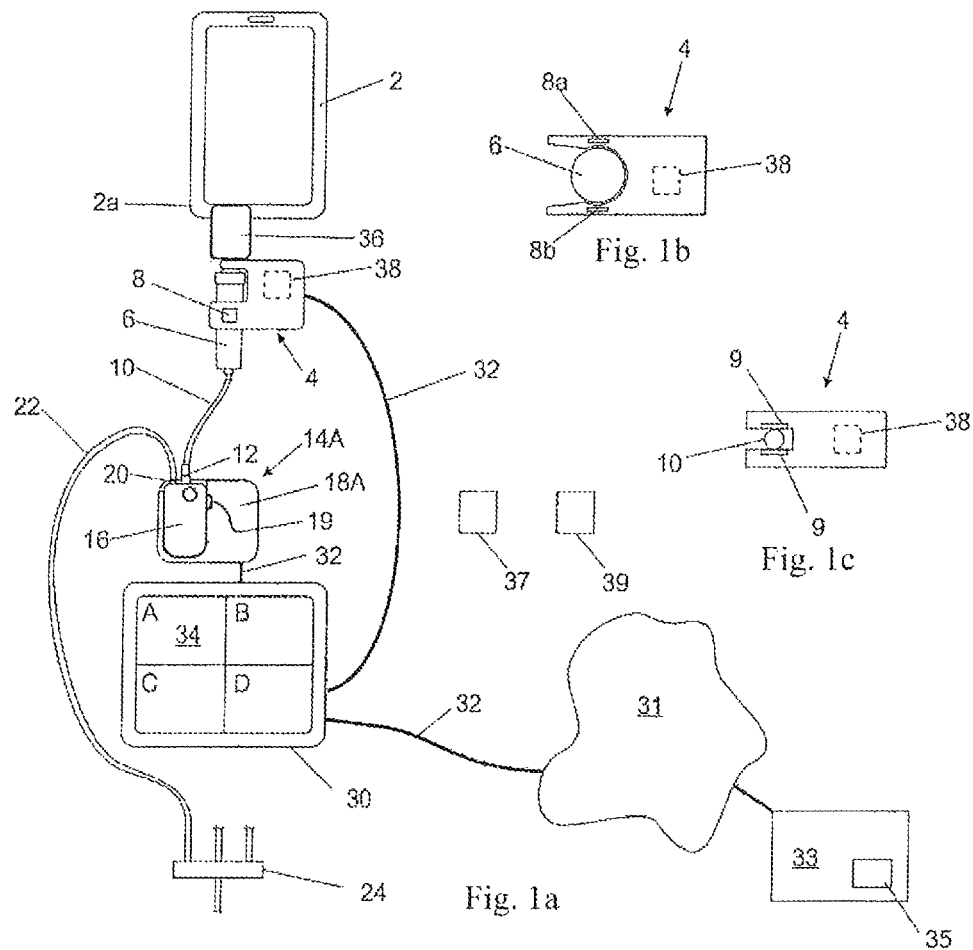
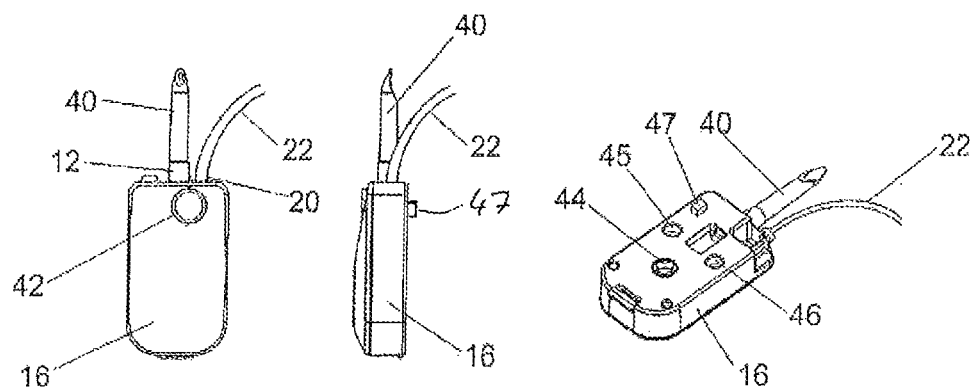

MEDICATION INFUSION SAFETY DEVICE AND A MEDICATION INFUSION DEVICE COMPRISING THE MEDICATION INFUSION SAFETY DEVICE

CROSS-REFERENCE TO RELATED APPLICATIONS

This patent application is a continuation of U.S. application Ser. No. 14/832,187, filed on Aug. 21, 2015, incorporated by reference in its entirety, such U.S. application Ser. No. 14/832,187 claiming the benefit of priority to European Patent Application No. 14181804.7, filed on Aug. 21, 2014.

FIELD OF THE INVENTION

The present invention relates to a medication infusion safety device for assuring an application of a correct medication to a patient, as well as a medication infusion device comprising the medication infusion safety device.

BACKGROUND OF THE INVENTION

Conventionally, an infusion pump is attached to a pole essentially at the level of the patient's bed, while a medication reservoir is suspended from a bar hook on the top of the pole, as disclosed e.g. by US 20150001285 A1 for a multi-pump system. In case a plurality of medication reservoirs and pumps are used wherein a high number of tubes are connected to the medication reservoirs and the pumps, it is difficult to find out which medication reservoir is associated to which pump, so that the monitoring or adjusting of the infusion of the correct drug is problematic, resulting in frustration and medication errors whereby more than 700 people in the U.S. are killed per year. Barcoding techniques try to remedy this in the prior art.

Syringe pumps instead do not have upstream lines, but themselves include the drug so as to have much better control. Therefore, such syringe pumps are used for critical drugs and in operating rooms because of their simplicity, infusion line mass avoidance and accuracy. However, they have still a big size problem. Namely, the use of several syringe pumps can result in the provision of a long stack (e.g. one meter long) one over the other, which is not appreciated in operating rooms. Whereas a transfusion into a syringe is needed, readily available pre-filled drug bags are available whereby a direct infusion is achieved through a high accuracy peristaltic pump.

When an operation is finished, a pole with pumps and drug bags accompanies the transportation of the patient to recovery, requiring personnel. There is a need for a pumping system which has the facilities of a bedside pump, but is also able to correctly operate as an ambulatory device and to be of minimum size.

Conventional multi-pump pole arrangements comprise pump modules provided with specific designations, e.g. referenced by letters "A", "B", "C". For programming the user needs to see to which drug a certain pump is to be connected—a method which is prone to medication errors as also recognized in the literature. Barcode systems try to correct this, but need attention when scanning a drug bag and visually checking the fluid connection to its associated pump, so that the risk of an error is not really eliminated. However, it must be assured that a medication or drug for a specific patient is infused under application of the correct protocol, which can be achieved due to the detection of the medication or drug by providing the medication reservoir with a visually readable or machine readable label, whereas the correct fluid connection to the infusion pump unit using the protocol must be assured either.

U.S. Pat. No. 7,976,508 B2 discloses a medication safety system wherein the medication reservoir or drug bag as well as the connected tube are subject to vibrations, while US 2014/0324019 A1 discloses an infusion data communication system wherein a very weak RFID signal propagates through the tubing. However, both these prior art systems may be difficult to implement without false alarms at low cost.

It is an object of the present invention to provide a medication infusion safety device and a medication infusion device which completely eliminate the possibility of wrong drug infusion and allow reliable and repeatable results.

SUMMARY OF THE INVENTION

In order to achieve the above and further objects, according to a first preferred aspect of the present invention, there is provided a medication infusion safety device for assuring an application of a correct medication to a patient, comprising a memory means adapted to be provided at a medication reservoir (3) containing a medication and to store data identifying said medication, a memory reading means adapted to be provided at an infusion pump unit and to read data from said memory means, and control means adapted to control an infusion in accordance with an evaluation of data read by said memory reading means so that only in case the evaluation leads to the result that the medication is correct it causes the infusion from said medication reservoir to be started, wherein said memory reading means is adapted to read data from said memory means through direct wireless connection and to be enabled to read data from said memory means in case the infusion pump unit is coupled to the medication reservoir with a distance between said memory means and said memory reading means being equal of or lower than a predetermined maximum wireless reading distance, further characterized by a fluid connection detection means which is adapted to detect the fluid connection of the medication reservoir to the infusion pump unit and to transmit to said control means a signal indicating whether or not the medication reservoir is connected to the infusion pump unit, and said control means is adapted to control an infusion additionally in accordance with the signal from the fluid connection detection means so that in case the evaluation leads to the result that the signal from the fluid connection detection means indicates that there is no connection of the medication reservoir to the infusion pump unit it causes the operation of the infusion pump unit not to be started or, if already started, to be, preferably immediately, stopped.

The provision of a fluid connection detection means according to the present invention has the advantage that the control means enables the infusion pump unit to operate and, thus, the infusion to be carried out only in case of two conditions, i.e. (1.) the correct medication or drug is provided for the specific patient (due to the detection of the correct medication reservoir by the memory reading means), and (2.) the infusion pump unit is fluidly connected to the correct medication reservoir (due to the detection of the correct connection by the fluid connection detection means). If at least one of both these conditions is not met, the control means prevent the infusion pump unit from operation and, thus, the infusion from being started, or, if the operation of the infusion pump unit and, hence, the infusion has already been started, causes the infusion pump unit to be immediately stopped. So, it is assured that only the correct medication or drug is delivered by the correct infusion pump unit for infusing the specific patient. Therefore, the memory means can also be called a medication identification means or medication reservoir identification means, and the fluid connection detection means can also be called a fluid connection assurance means. After all, due to the present invention it is successfully and safely avoided that a wrong medication or drug is applied to a specific patient for infusion.

Preferred embodiments and modifications of the present invention are defined in the dependent claims.

Preferably, said memory reading means is adapted to be positioned close to said memory means without being any upstream tube or any other space creating and disturbing element between medication reservoir and infusion pump unit.

Preferably said fluid connection detection means is adapted to be provided adjacent to or at an outlet port of the medication reservoir.

According to a preferred embodiment of the present invention, said fluid connection detection means comprises flow sensing means, preferably associated with pump rate alteration means, and/or a flow control valve associated with upstream and/or downstream pressure sensing means which are adapted to detect a flow of the medication from the medication reservoir to the infusion pump unit, wherein said signal output by said fluid connection detection means and indicating whether or not the medication reservoir is fluidly connected to the infusion pump unit is a signal indicating whether or not the medication is flowing from the medication reservoir to the infusion pump unit in particular according to commands from the infusion pump unit. Usually, the flow rate as detected by the flow sensing means and the check of the memory means is continuous during the infusion, so that any unintentional change results in an alarm or other action.

According to a further preferred embodiment the infusion pump unit includes a pump comprising an inlet port which is adapted to be directly fluidly connected to an outlet port of the medication reservoir, wherein said memory reading means is adapted to be provided at the pump. So, this embodiment provides for a direct fluid connection with the lack of any upstream tube between the pump and the medication reservoir (or at most with the provision of only a very short upstream tube). Since the memory reading means is provided at the pump which due to the direct fluid connection is to be positioned close to the medication reservoir, in this embodiment the memory reading means is brought into close vicinity with memory means at the medication device resulting in short and therefore safe reading distance.

According to an alternative preferred embodiment, the infusion pump unit comprises a pump, an upstream tube whose outlet is coupled to an inlet port of the pump, and a connection check module provided at the inlet of the upstream tube and adapted to be fluidly connected to an outlet port of the medication reservoir, wherein said memory reading means is adapted to be provided at the connection check module. As the provision of an upstream tube between the medication reservoir and the pump results in a (more or less) long distance exceeding the maximum reading distance which would render a safe reading of the memory means at the medication reservoir by the memory reading means impossible, in this embodiment the memory reading means is not provided at the pump but is to be positioned separately and away from the pump close to the medication reservoir in order to ensure a short and safe reading distance to the memory means at the medication reservoir. This is realized by arranging the memory reading means at the connection check module which is provided at the inlet of the upstream tube and adapted to be fluidly connected to the outlet port of the medication reservoir. According to a modification of this embodiment, the fluid connection detection means can also be provided at the connection check module so that a combination of the memory reading means and the fluid connection detection means are provided at the connection check module.

According to a still further alternative preferred embodiment, the infusion pump unit comprises a pump and a plurality of upstream tubes whose outlets are coupled to an inlet port of the pump wherein there are provided a plurality of medication reservoirs corresponding in number to the plurality of upstream tubes, wherein at the inlet of each upstream tube there is provided a connection check module which is adapted to be fluidly connected to an outlet port of a medication reservoir, further comprising a plurality of memory reading means and a plurality of fluid connection detection means, wherein a combination of a memory reading means and a fluid connection detection means is adapted to be provided at a connection check module at the inlet of each upstream tube. This embodiment is particularly appropriate for a piggyback infusion configuration.

According to a further preferred embodiment, the pump comprises a first part, preferably a consumable first part, which includes a pump mechanism and is provided with the inlet port, and a second part including a motor for driving the pump mechanism of the first part, wherein the first part is releasably attachable to the second part for operation of the pump, further comprising a detecting element, preferably a switch, which is adapted to output a signal indicative of whether or not said fluid connection check module is needed, and further comprising sensing means, in particular upstream pressure sensing means, which is adapted to output a signal indicative of whether or not the first part and the second part are attached to each other so as to complete the pump to be ready for operation, and wherein said control means is adapted to evaluate the signal from the memory means and the fluid connection detection means only in case the signal from said sensing means indicates that the first part and the second part are attached to each other.

Preferably, there is provided a body which is adapted to be fastened to an outlet port of the medication reservoir wherein said memory means is provided at said body or consists of said body. Said body may comprise fastening means for releasably fastening the memory means at the outlet port of the medication reservoir wherein the fastening means may comprise a clamp. This embodiment provides for sufficient stiffness and robustness for a good handling and for multiple re-use and disinfection procedures of the memory means.

According to an alternative preferred embodiment there is provided a body which is adapted to be fixed at a lower edge portion of the medication reservoir so as to protrude or be suspended from the medication reservoir, wherein said memory means is provided at said body or consists of said body. This embodiment provides for a convenient way of arranging the memory means at the medication reservoir and assures in a particular safe manner that the memory means is located within the reading distance.

According to an advantageous modification of this embodiment, the said body is adapted to be integral with a medication reservoir.

Moreover, said body can comprise a plate on which the memory means is provided.

Preferably, the memory means comprises a label or tag, in particular a smart label or tag, preferably a RFID, wherein the memory means may additionally comprise a powerless display element, preferably an electronic paper element. Preferably, the powerless display element is programmable, wherein the programming can be powered by wireless energy, and the powerless display element can get data from an RFID/NFC memory tag which receives radio frequency power from an RFID programmer based on a personal computer or a mobile phone so that the complete visual tag system needs no battery.

Preferably, the control means may be part of the infusion pump unit or of the pump being part of the infusion pump unit wherein this solution provides for a smart infusion pump unit or pump in particular due to the integration of some more intelligence in form of hardware and software.

Alternatively, the control means may define a separate device or may be part of an external server whereby most of the intelligence in form of hardware and software does not need to be implemented into the infusion pump unit or the pump. So, this solution provides for a more simple configuration of the infusion pump unit or the pump. In particular if the control means is embodied as a separate device, it is preferably adapted to be located essentially near the patient's bed and, if required, to be connected to an external server as well.

According to a further preferred embodiment, there is provided a second memory means adapted to be provided at the patient and to store data identifying said patient, and a third memory means adapted to be provided at the patient's bed or in the care area or room where the patient's bed is situated and to store data identifying said location or said room, wherein said memory reading means is adapted to also read data from said second and third memory means.

According to a further preferred embodiment, there are provided access means for enabling said control means to have access to a drug and protocol library and an electronic prescription provided for the patient, wherein said control means is adapted to control an infusion in accordance with the evaluation of data read by said memory reading means and data from said library and the electronic prescription so that in case the evaluation leads to the result that the medication and protocol each are correct for the specific patient it causes the infusion from said medication reservoir to be started.

According to a still further preferred embodiment, there is provided a plurality of infusion units wherein each infusion unit is connected to a medication reservoir and comprises an infusion pump unit, a memory reading means and a communication means for communicating with said control means, and wherein said control means comprises a plurality of a controllers which are adapted to control said infusion units independently from each other in accordance with the evaluation of data read by said memory reading means so that only in case the evaluation leads to the result that the medication and preferably also a medication protocol, is correct for the specific patient, and the connection to the infusion pump unit, preferably running the medication protocol, is verified for infusion by means of a specific infusion unit it causes said specific infusion unit to operate so as to start infusion from the medication reservoir connected to said specific infusion unit.

According to a still further preferred embodiment wherein a plurality of reservoirs are all commonly connected to one infusion pump unit, the control means is adapted, in case signals from the fluid connection detection means indicate that there is a change of flow from one reservoir to another reservoir, to stop the operation of the infusion pump unit by giving a warning and waiting for action of an operator or to cause the operation of the infusion pump unit to be continued in accordance with the protocol associated to the other reservoir preferably by giving a warning.

According to a second aspect of the present invention, the above object is achieved by the provision of a medication infusion device for infusion of a medication or drug into a patient, comprising a medication reservoir, an infusion pump unit and a device according to the first aspect of the present invention.

A preferred embodiment of the medication infusion device comprises a plurality of medication reservoirs, a plurality of infusion pump units and a support structure, preferably a rack, supporting the plurality of medication reservoirs in an inclined orientation, preferably side by side, wherein the infusion pump units are located adjacent to the lower end portion of the medication reservoirs with each infusion pump unit directly coupled to a different medication reservoir. Moreover, the infusion pump units may also be supported by said support structure.

According to a further preferred embodiment of the medication infusion device an infusion pump unit is wirelessly connected with other infusion pump units, the control means and/or a charger for charging power.

According to a still further preferred embodiment of the medication infusion device an automatic or on-demand infusion sequencing of multiple medication reservoirs fluidly connected to the same infusion pump unit is carried out by the connection detection means on the same module with the memory reading means provided at the outlet port of each reservoir enabling or disabling the flow, and with the use of infusion protocols associated to each medication and time or volume limit to switch from one infusion to the next infusion.

After all, the present invention provides a safe drug-for-infusion protocol under strict consideration of the "5R" validation rule ("right patient", "right drug", "right dosing", "right delivery route", "right time"), an improvement on reservoir the and tubing management in case of multiple infusions, less space requirements for a multiple infusion management, and an improved portability for the patient.

The data for all drugs or medications to be infused to a patient can be downloaded to the pump system from an electronic health record system which usually comprises a server via interoperability standards so that a validation can be carried out one by one when connecting. The patient can be scanned or questioned about his identity so that an error to infuse to a wrong patient can be eliminated. A drug or medication is contained in a bag or reservoir, and since its memory means or label is read it is assured to have the correct drug or medication.

Preferably, the infusion pump comprises a consumable part with a spike which connects a drug bag to a patient with the provision of an upstream tube until the pumping segment introduced into the pump and a downstream tube to a multi-line connector and then to the patient.

The problem is how to assure that the spike connector with a tube coming from the pump (which is programmed to operate by a correct infusion protocol for a specific one of the drugs to be infused) has really been connected to the correct bag or reservoir containing the drug or medication which the pump intends to infuse. If you have a medication label read electronically and there are many reservoirs and many pumps, how do you know that the infusion line goes to the pump with the correct protocol?

Due to the present invention, there is provided a solution with two variations for overcoming this critical problem. It is needed to detect the medication or drug attributes and at the same location (at minimum distance from the next medication reservoir and at maximum distance from a detector) to automatically verify the upstream connections reservoir-spike-pump directly or indirectly.

According to a preferred embodiment of the present invention, a memory reading means is provided close or together with connection verifying means so as to assure that the infusion pump unit is connected to the correct medication reservoir. For doing so, there are two preferred equivalent solutions.

In case of a first solution, there is no upstream tube between the medication reservoir and the infusion pump unit wherein the spike of the infusion pump unit (which spike is preferably provided at a pumping cartridge and defines its inlet port) is directly connected to the medication reservoir. So, the memory reading means provided on the infusion pump unit or module is very close to the memory means at the reservoir. That is to say that the infusion pump unit is practically on the medication reservoir with its memory means being read by the memory reading means. As a result, the link "correct protocol" to "correct drug" is assured since information on the medication (as stored in the memory means which preferably is a tag or label) and infusion (as carried out by the infusion pump unit) are on the same location not allowing any confusion or errors.

According to a second solution, not only the medication is recognized by reading the associated memory means at the reservoir, but also the flow through the infusion line on the same module is detected and/or controlled. In this case, the infusion is proceeded if not only the correct medication but also the correct reservoir-to-pump connection is verified in particular through control by infusion pump flow attributes. If the infusion pump unit is started to operate, but a flow through the infusion line leading to said infusion pump unit has not started, at once the operation of said infusion pump unit is finished again in order to avoid that a wrong medication from a different and wrong reservoir is to be infused. Alternatively, in case a tube valve is provided, this valve may close the flow at the start of infusion, wherein an upstream occlusion is detected preferably by the fluid connection detection means or by the infusion pump unit so as to verify that the fluid connection to the medication reservoir is indeed closed, whereupon the valve opens again in order to continue the infusion according to the verification of the correct connection, or in case of a wrong connection an alarm is given. Such occlusion detection may be done at maximum speed of the infusion pump unit and for a calculated maximum volume up to an alarm, in particular for test purposes.

According to a preferred aspect of the present invention, the infusion pump unit with its memory reading means is any time in contact or very close to the memory means which may be provided as an instruction label and is arranged at some portion of the medication reservoir and preferably at an edge of the medication reservoir. Preferably, the memory means communicating with the memory reading means at the infusion pump unit comprises a RFID label, a NFC label, a barcode label, contact points to an on-label memory chip or a conductive print binary code label. A contact readable memory can be printed by organic electronics methods (printable electronics) as known in the art. Preferably, a memory label of any of the above mentioned technologies may protrude from the medication reservoir like an edge or bordersheet down towards the location of the infusion pump unit near its inlet port or spike which either is provided at the inlet port or forms the inlet port. Preferably, the memory means may also comprise a ring to be provided around the tube at the outlet port of the medication reservoir to be spiked close to the positioning of the spike. So, preferred locations of the memory means may be at the tube or at the medication reservoir outlet port close to the lower edge of the medication reservoir or at the medication reservoir close to its outlet port to be coupled with the tube or the spike or luer connector of the infusion pump unit.

By this way, some or all of the "5R" safety rules are checked by the control means which may be implemented in the infusion pump unit or in a separate device. Moreover, further infusion related information, namely a drug name, concentration, diluter, infusion protocol and limits from a drug library, patient's name, age and location or room number, administration route, time to infusion, air-in-line and infusion occlusion pressure preferences for alarm can be written in the memory means for a patient in particular by the hospital pharmacy or an external drug compounder or manufacturer.

Preferably, the infusion pump unit comprises a consumable cartridge which includes a rotary peristaltic pumping mechanism and is made of plastic with a weight of a few grams only. So, such an infusion pump unit comprises two parts, namely a first part forming said consumable cartridge and a second part forming the (remaining) pump module. By using such an infusion pump unit there are two options for the aforementioned first solution.

One option is that the second part or pump module only includes the motor for driving the pumping mechanism in the first part or consumable cartridge as well as electronics and optionally also a display, but no keyboard, no battery and no buzzers, wherein the pump module is connected only by a cable to a stationary IT system. The first part or consumable cartridge also comprises the spike and can be safely hanged by the spike at the exit port of the medication reservoir. The second part or pump module fits to the first part or consumable cartridge and includes all electronics for operating the infusion according to the protocol and for measuring upstream and downstream pressure and air in line as well as the memory reading means for drug recognition and reading instructions from the memory means. In case the memory means comprises an RFID, the memory reading means can also have a writing function so that when the pumping function is stopped or the infusion pump unit is in a standby mode it writes the volume to be infused, the protocol and a possible infusion error into the memory means, so that another infusion pump unit can take over the infusion by using the same consumable cartridge and downloading from the memory means all necessary information to resume the infusion. The cable with the pump module can be hanged from a hook of the medication reservoir by an elastic, free spring or miniature rotary spring tool balancer, easily picked and fitted on the consumable cartridge after connecting (spiking) and priming the medication reservoir.

The other option is that a complete infusion pump which can also be very light weight can be used by being hanged from the consumable cartridge or its spike.

A still further option is that the above mentioned consumable cartridge is already factory fitted at the medication reservoir including a pre-filled drug, so that the pump module is to be fitted to the cartridge at the medical reservoir in close contact with the memory means provided at the medical reservoir.

The medical reservoir can be hanged higher on a pole or just below a horizontal monitoring bar where a display and a keyboard are located for all infusion pump units used for a patient. In the latter arrangement, any size of medical reservoir can be accommodated (having different size below the bar) while all displays are on the same level at the bar wherein each local display is arranged over its associated medical reservoir and a further display is provided for controlling all the pumps at the pole center.

The medication reservoir can also not be hanged, but laid down on an inclined rack or shelf, wherein air in the reservoir can still go up while the medication reservoir has enough friction on the rack so as not to slip downwards. Further, at a border bar below, a pump controller is fixed which also serves somewhat like a stop for the medication reservoir or bag in order to avoid it to fall down to the floor, wherein the rack or shelf may additionally be provided with a stop against which the lower edge of the medication reservoir is to be abutted. This is a good solution for syringe pump replacement where bag volumes are small (in particular 50 to 100 ml). Further, on the front of the shelf or rack a display shows drug and protocol for the infusion. In such a case, even eight pumps together take the place of one or two conventional syringe pumps. Also in this arrangement the memory means at the medication reservoir is always in contact with the memory reading means at the infusion pump unit.

For the above mentioned second solution (with the provision of an upstream tube), according to a further preferred aspect of the present invention, the inlet port or spike of the infusion pump unit is provided with a drip chamber at which a combination of a drip flow monitor and a memory reading means like an RFID reader can be attached so as to read the memory means like an RFID label at the medication reservoir. Also in such an arrangement, the memory means can extend or protrude from the lower edge of the medication reservoir so as to be closer than a predetermined maximum distance from the position of the memory reading means. Further, a cable connects the combination of the drip flow monitor and the memory reading means to the infusion pump unit, the control means and an IT part of the system.

According to another preferred aspect of the present invention, the infusion pump unit is not always programmed at the pole, but rather at least the pump module can be programmed at the pharmacy, in the nurse room or in the doctors office and then transported to the patient's location. Also in such an arrangement the infusion pump unit consisting of the pump module and the consumable cartridge has full bedside pump capabilities like a rate of 1000 ml/h at very low noise with upstream and downstream occlusion detection and air-in-line ultrasonic detection, WiFi and RFID communication and extremely low power consumption so that a charged battery has power for all days of a patient in a hospital (usually about four days).

A further preferred aspect of the present invention is that huge IT functions of a bedside pump system are split from the pumping functions of the infusion pump unit mounted at the pole, i.e. comprising a tablet touch type of computing device with accessories such as a conventional laser barcode reader, or a tablet or phone camera based barcode reader, on-screen medical personnel signature storage, biometric analysis and documentation, the provision of voice commands, which complete an enhanced electronic record documentation, wired or wireless charging capability of many ambulatory infusion pump units, and hospital network connectivity and interoperability. So, e.g. a tablet as a part of the IT system at the pole, further provided with emergency batteries, controls in particular 1 to 8 ambulatory infusion pump units and displays infusion parameters, in particular in separate windows, in a controlled-by-lighting-conditions (night/day, light on/off) LCD or AMOLED color display to be seen from far away when appropriate.

Special gestures like opening by two fingers or tapping on the screen or a voice command may increase one of the windows to a larger size or to full screen so that a full control of the infusion pump unit can be done by the tablet, whereas reverse hand gestures or voice commands may reduce the window to a smaller size again so as to have the display of the multiple pump arrangement again. For hands free voice commands, a foot paddle switch may be connected to the IT part of the pump system so as to be pressed for activation of voice commands such as "pump A" for the first pump, whereas the IT system displays the full screen protocol and status. When pressing the foot paddle switch and speaking the command "rate 234.5", the IT system displays a rate of 234.5 ml/h. Then after showing the correct value at the display, the foot paddle switch is pressed and the command "start rate" is spoken so that the infusion pump unit receives the new rate from the IT system and starts running, while the IT system display returns to show the multi-pump arrangement again. A similar hands-off user interface for operating rooms is a hand gestures detecting radar now available as a single chip solution. So, for instance the adjustment of the rate can be done by sliding two fingers, the operation can be started by tapping two fingers twice, and the pump selection (1/4) can be done by tapping one of four fingers by a thumb.

According to another preferred aspect of the present invention, a safe multi-stage communication way can be implemented, where the memory means at the medication reservoirs are validating and closing the safety loop. IT systems due to their complexity are hard to certify as a safe medical device, whereas the present invention provides means to reduce the risk of such use. Namely, an infusion management application running on the IT system does not allow other applications to be downloaded wherein a so-called daemon runs on a thread to check the running programs and kills any application which is not registered. Furthermore, a frequent regular communication between the IT system and the medical device can give the medical device the role of an external watchdog to check the performance of the IT system so that in case of a problem an alarm from the medical device is issued, while the continuation of the infusion process and the use of a local user interface make sure that life support infusions in operating rooms and intensive care units are flawless. This function is a result of separation of infusion functions from IT functions as it is possible due to the present invention.

Due to the present invention the hospital automation and electronic health record management can be easily managed by communication between the medical devices and the IT system, too. In each communication between devices, there are steps of sending back information for verification and confirmation for safety reasons so as to allow and certify the use of non-medical devices to participate in medical functions. A doctor writes on a personal computer or mobile device an e-prescription which in particular includes the patient's name, care area and room number and is sent to a remote server for storage in a database. The e-prescription is used by the pharmacy to prepare a medication reservoir accordingly and to print upon the memory means such as a memory label, preferably an RFID tag, the drug name, the volume, the concentration, the diluter, the patient's name, age and room number, the rate to be infused or a more complex protocol, the drug library limits, the administration route, and the time to deliver. The memory means is attached to the medication reservoir, preferably at its bottom, close to its outlet port by a pharmacist as a competent authority.

The server shows if there is a pole-mounted IT system positioned close to the patient's bed or not. In case there is an available pump (not yet used), the protocol is sent to a bedside IT device. If there is no available pump, a fully recharged infusion pump unit at the site of the pharmacy receives the protocol and gives an indication, in particular by a blinking optical signal, that it is ready to deliver, so that it is taken by a nurse together with a medication reservoir and the infusion set.

In case of a so-called stand-alone infusion without a pole IT system, the consumable cartridge is spiked into and, thus, connected to the outlet port of the medication reservoir, and the pump module is attached to the cartridge. The so completed programmed pump displays the patient's name, the care area and the room number as well as the name of the medication or drug for safety reasons. Since the pump with its pump module including the memory reading means is arranged in close vicinity or in contact with the memory means, the pump validates the protocol and the "5R" rule by evaluating the data received from the reading of the memory means by the memory reading means for safety reasons in order to avoid the application of a wrong drug or medication. A mobile application can check the patient's label and a further label at the pump wherein both these labels can be a barcode, or the pump itself can scan the patient's label which preferably can be a RFID label in particular when the pump is embodied as a miniature pump. In such a case, questions about the delivery route are responded, the time is checked, information is sent to a server, the server confirms that patient and protocol on the pump are correct, in particular also fully in view of the "5R" rule, and also sends a "5R" compliance to the infusion pump (which is WiFi enabled) to allow infusion without medication errors. The care area is connected to a drug library storing therapies, allowed infusion protocols and special configuration parameters such as alarm point display illumination preferences in particular to be shown on the pump monitor or the nurse' monitor, wherein the correct care area needs to be validated. The exact position of the care area can be automatically retrieved through geolocation by using the WiFi strength or specific labels in the room to be scanned by the pump or a mobile application, or by selection from a list on the pump or the IT system at the pole to be validated by the nurse.

In case of the provision of a bedside pole IT system communicating directly to several infusion pumps, the same procedure is carried out, but no external mobile application is mandatory which rather is embedded in a tablet defining part of the IT system. The only difference is that the tablet sends the protocol received from the server after preparation by the pharmacy to a specific pump which acknowledges the data from the memory means at the medication reservoir, i.e. from the drug label, as used in the specific protocol, so that a correct protocol-pump-medication link is guaranteed.

By splitting the function of infusion devices from the function of IT devices, it is up to the infusion devices which have the decision to infuse by checking all parameters for consistency. Even, there may be a separate infusion device for each drug or medication so that critical care for life support has less chances to fail since all devices are different and independent from each other so that the pumps can run independently, even separated from the IT system, and be put on the bed for transportation during the infusion. Of course, there may be also an option where the IT system or at least the tablet is a medical device itself as a trustable part in a regulatory medical system.

Below there are described communication steps for a tablet type IT system directly provided at the pole and having a communication with each of the pumps at the same pole mount, and for a remote server which forwards an e-prescription from a remote doctor to the pharmacy for the preparation of the medication reservoir and the memory means (drug memory label), wherein a protocol is communicated to the IT system identifying the system dedicated to the specific patient and mounted at a specific pole from the patient's name and room number, or directly to an infusion pump unit (in particular in case it comprises a single miniature infusion pump with WiFi connectivity) while the infusion status is regularly returned back and displayed for all pumps at the poles in any remote location including a nurse attendance desk. The IT system receives the protocol, and once an infusion pump unit gets a label message of the drug by reading the content of the memory means by the memory reading means wherein the medication reservoir has been positioned or hanged close to one of the several pumps, the infusion pump unit also receives the protocol of the drug from the IT system, in particular from the IT tablet, and checks the identity of said protocol in view of the protocol received from the memory means for safety and redundancy reasons.

A safe multi-stage communication may have four steps when initiated by the IT system and three steps when initiated by the medical device. The communication between IT systems uses cyclic redundancy check (CRC) and forward error correction (FEC) algorithms wherein the message is enlarged by some bits to correct communication errors, as required in high speed communication. The content of the communication between medical devices is usually very small so that it can be sent back for checking its integrity, giving the highest level of security.

A communication initiated by the IT system is as follows:
Step 1: A message such as protocol or start infusion order etc. is sent by the IT system
Step 2: The medical device checks the integrity or validity of the message at the status of operation and, if function is enabled or disabled, sends back the same message to the IT system if ok or an error code if not.
Step 3: The IT system compares the sent and received messages for identity, and if yes sends an "OK" and if not re-sends the message as in step 1.
Step 4: The medical device starts using a validated command and sends a status command in use.

A communication initiated by the medical device:
Step 1: The medical device sends a status message to the IT system.
Step 2: The IT system stores values, retrieves stored values and sends them back to the medical device for verification, and if the result of the verification done by the medical device is ok the medical device sends an "OK" to the IT system.
Step 3: The IT system displays values in case of the receipt of "OK", but if there is no "OK" erases stored values.

A further preferred aspect of the present invention deals with the provision of pairs of medications and protocols given in an e-prescription to be downloaded from an external database for a specific patient and associated to predetermined limits of a specific care area. In case of a multiple medication infused by a single infusion pump unit, the number of the upstream tubes must be equal to the number of the medication reservoirs. Clamps are provided for manually closing and opening the upstream tubes wherein for an infusion all upstream tubes are clamped except for one upstream tube which is left open for the medication reservoir desired for infusion, and then in accordance with the medication or drug flowing through said open upstream tube a corresponding protocol is chosen, or in case the medication reservoir desired for infusion is determined by its height, only said desired medication reservoir is to be located higher than all the other medication reservoirs, resulting in that no clamps are needed. In such a configuration, by using the memory means and the fluid connection detection means according to the present invention, it is detected which medication is delivered, and in accordance with the result of the evaluations by the control means the correct protocol is automatically applied.

Alternatively, each upstream tube can be provided with an active valve so that there are a number of valves equal to the number of the upstream tubes. Preferably each valve can be arranged at the same unit as the memory reading means. The valves are controlled by the control means so as to allow an automatic sequencing of infusion, by closing all the valves except for one valve which remains open for the upstream tube coming from the desired medication reservoir, wherein according to the associated protocol in particular specifying volume and/or time the infusion is carried out. This is very important for chemotherapy infusions wherein a plurality of drugs, in particular as many as seven drugs, are sequenced one after the other for a specific patient. With respect thereto, it is to be reminded of, as already mentioned above, that the control means can be integrated into the infusion pump unit or be part thereof or be provided as separate device. Said active valves may be preferably part of said fluid connection detection means, wherein for verification of the connection first all the valves close, then the infusion pump unit starts running at high speed until an upstream occlusion occurs or the maximum test volume is reached, and thereafter without giving an alarm the valve opens at the desired upstream tube connecting the desired medication reservoir to the desired infusion pump unit operating according to the desired protocol, so that the upstream pressure is going back to a normal amount, and, if sensed, preferably by the fluid collection detection means or the infusion pump unit, then a normal infusion protocol starts. However, in case the maximum test volume is reached, an alarm is given for wrong fluid connection. Due to such a system it is assured that a spike of another infusion pump unit supported by the same pole is not fluidly connected to a medication reservoir of the sequence or piggyback infusion. Such an upstream occlusion test may alternatively result in a shorter detection time and volume, as determined by reaching the maximum volume (in case the valve is not closed), but also for low pressure reading (in case the valve is closed). So, a simple pressure decay and slow evaluation algorithm may be sufficient well before the occurrence of an occlusion alarm value, also in case of an open valve since there is no decay.

According to a preferred aspect of the present invention, a safe infusion needs the provision of memory means for the detection of the content of a medication reservoir to be delivered and the provision of fluid connection detection means for checking the correct connection of the medication reservoir to the infusion pump unit wherein the associated correct protocol (the pair of the medication) is to be applied for the specific patient.

According to a preferred embodiment, in the fluid connection detection means there may be implemented three functions, i.e. (1.) checking whether the medication reservoir is fluidly connected to the infusion pump unit directly or via an upstream tube, (2.) detecting whether or not a flow of medication or drug from the medication reservoir is started, and (3.) detecting a possible upstream occlusion. So, there are three ways to use such a combination of the memory means and the fluid connection detection means as follows:

1. Since the fluid connection detection means detects that the medication reservoir is directly fluidly connected to the infusion pump unit without the provision of any upstream tube there between, no further detections are needed.
2. If the medication reservoir is fluidly connected to the infusion pump unit via an upstream tube, the fluid connection detection means is looking for whether or not the flow of the medication or drug from the medication reservoir is started when the pump is started to operate.
3. If the medication reservoir is fluidly connected to the infusion pump unit via an upstream tube and a valve is provided for closing and opening said upstream tube, the fluid connection detection means uses a detection of occlusion in the upstream tube for verifying the connection wherein the valve is closing the upstream tube just during the start of the operation of the infusion pump unit and is releasing it just after a detection of occlusion in the upstream tube.

The aforementioned and other advantages of the present invention will become apparent from the following more detailed description when taken in conjunction with the accompanying drawings of illustrative embodiments.

BRIEF DESCRIPTION OF THE DRAWINGS

FIGS. 1a-c show a medication infusion system comprising a medication infusion safety device according to a first preferred embodiment (a) and a cross-sectional view through a fluid connection check module according to a first variation (b) and according to a second variation (c);

FIGS. 2a-c show a consumable pump cartridge including a pump mechanism in a front view (a), a side view (b) and a perspective view (c);

DESCRIPTION OF PREFERRED EMBODIMENTS

Figure 3:
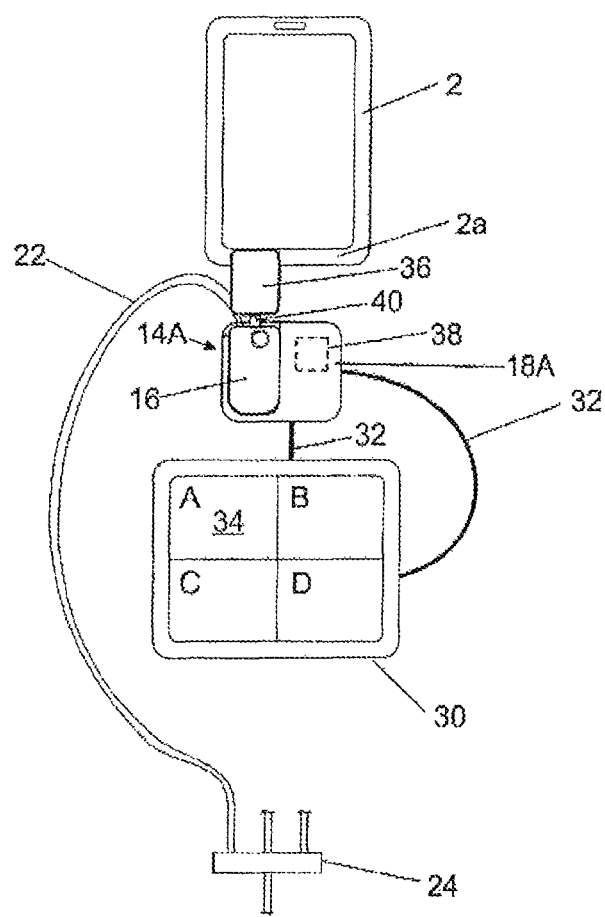
FIG. 3 shows the medication infusion system comprising the medication infusion safety device according to a preferred second embodiment.

FIG. 1a schematically shows a medication infusion system according to a preferred first embodiment. The system comprises a medication reservoir 2 which at its lower edge portion 2a is provided with an outlet port (not shown in FIG. 1a-c). For infusion, the medication reservoir 2 is filled with a specific medication or drug. At the outlet port of the reservoir 2 there is provided an electronic fluid connection check module 4 which is attached to an arrangement of a drip chamber 6 and a spike (not shown) fluidly connected to the outlet port of the reservoir 2 and comprises a flow sensor 8 which is provided as a so-called drip detector in the shown embodiment. As shown in FIG. 1b, in the depicted embodiment the portion of the connection check module 4 adjacent to the drip chamber 6 has a cross section like a U and, thus, partly surrounds the drip chamber 6 which is configured as a cylinder. As further seen from FIG. 1b, the flow sensor 8 comprises two elements 8a and 8b which are arranged opposite to each other with the drip chamber 6 therebetween wherein one of the sensor elements 8a, 8b is a transmitter for emitting an optical or electromagnetic beam and the other one of the elements 8a, 8b is a receiver for receiving the optical or electromagnetic beam. During infusion, the flow sensor 8 detects the flow of the drug exiting the reservoir 2 through its outlet port and flowing through the drip chamber 6 so that the flow sensor 8 outputs a signal indicating whether or not the drug is flowing and, if yes, at which rate.

An upstream tube 10 is connected with its inlet to the outlet of the drip chamber 6 and with its outlet to an inlet port 12 of a pump 14A. In the shown embodiment, the pump 14A is divided into two parts, i.e. a first part 16 including a pump mechanism (not shown) and a second part 18A only including a motor for driving the pump mechanism in the first part 16 and further hardware like control and detection electronics (not shown). According to the shown embodiment, the first part 16 defines a consumable pump cartridge which is preferably made of plastic resulting in low weight and low manufacturing costs. As further seen from FIG. 1a, the pump cartridge 16 is provided with the inlet port 12. The second part 18A defines the rest of the pump 14A and can also be called a pump module. The pump module 18A has an extremely low weight and a very small size so that it is not bigger than drip sensors of today's bedside pumps and is sufficient to fluidly connect to the reservoir 2 resulting in an extreme easiness of use and associated medication error prevention. The first part or pump cartridge 16 and the second part or pump module 18A are provided with attachment means (not shown) so as to be able to be attached to each other in order to provide the complete pump 14A as shown in FIG. 1a. As further schematically to be seen from FIG. 1a, the second part or pump module 18A is provided with a detecting element 19, which is preferably embodied as a switch and is adapted to detect the type of the pump cartridge 16 used and to output a signal indicating whether there is provided an upstream tube 10 as shown in FIG. 1a or a direct spike-to-reservoir connection without the provision of an upstream tube as shown in FIG. 3. The detection of whether or not the pump cartridge 16 is attached to the pump module 18A is done by upstream and downstream pressure detectors which output a corresponding signal.

As further shown in FIG. 1a, the pump 14A comprises an outlet port 20 which is provided at the pump cartridge 16 and fluidly connected to the inlet of a downstream tube 22 whose outlet is fluidly connected to a fluid collector 24 to be fluidly coupled to a patient.

As also shown in FIG. 1a, the system further comprises a controller 30 to which the connection check module 4 and the pump 14A are electrically connected via electrical cables 32. So, the controller 30 receives the signal from the flow sensor 8 and communicates with the pump 14A in particular for exchange of data and controlling the pump 14A wherein the controller 30 also receives the signal from the detecting element 19. The controller 30 comprises a display 34 which is preferably embodied as a touch screen, and there can be also a keyboard for writing into the controller 30 and a mouse (both not shown here).

As further shown in FIG. 1a, in the depicted embodiment there is provided a tag or a label 36 at the reservoir 2 whereas an associated tag or label reader 38 is included in the connection check module 4 as shown by dotted lines. The label reader 38 is able to wirelessly read data stored at or in the label 36 and to output a signal including such data which are transferred via the cable 32 to the controller 30. The data to be stored at the label 36 are data indicating the medication or drug contained in the reservoir 2. For a fluid connection of the pump 14A with the reservoir 2, the connection check module 4 can be releasably attached to the reservoir 2 so that the drip chamber 6 is releasably fluidly connected to the outlet port of the reservoir 2. In preparation of an infusion, among a plurality of reservoirs 2 filled with different drugs, a reservoir 2 including the desired specific drug is selected and fluidly connected to the pump 14A by fluidly coupling the drip chamber 6 to the outlet port of said reservoir 2. Each reservoir 2 is provided with the label 36 wherein the data stored in the label 36 give information about the drug or medication in the associated reservoir 2. So, the label 36 and the label reader 38 are provided for evaluation whether or not a reservoir 2 including the correct drug is connected to the pump 14A for infusion. As the data stored in the label 36 relate to the drug or medication filled in the reservoir 2, the label 36 is attached to the reservoir 2 so as to be assigned and associated thereto.

Since the reading distance is limited, the label reader 38 needs to be located as close to the label 36 as possible. Therefore, in the embodiment shown in FIGS. 1a-c, the label reader 38 is integrated into the connection check module 4 which is located close to the reservoir 2 and, thus, close to the label 36. Preferably, the label 36 comprises an RFID, and the label reader 38 is provided as an RFID reader. However, it is basically conceivable to use other constructions and embodiments for the label 36 and the label reader 38 to realize a wireless reading. Further, it is also conceivable that the label 36 and the label reader 38 are optical means so as to operate on an optical basis, e.g. by providing a barcode and a camera in particular with a slight modification of the design so that the label 36 and the label reader 38 face each other.

Inter alia the signals and data from the flow sensor 8, the detecting element 19 and the label reader 38 are processed by the controller 30. Instead of using the cable 32 shown in FIG. 1a, the communication between the controller 30 on the one hand and the connection check module 4 and the pump 14A on the other hand and in particular the transmission of data and signals from the flow sensor 8, the detecting element 19 and the label reader 38 can also be done in a wireless manner after having them paired before use. An important task of the controller 30 is to allow a complex programming and to control the infusion process and in particular the pump 14A. At the beginning of an intended infusion, the data from the label reader 38 are evaluated by the control means 30 so that only in case the evaluation leads to the result that the medication or drug in the reservoir 2 is correct it causes the pump 14A with the associated infusion protocol to be started. However, in case the detecting element 19 shows that there is an upstream tube 10 with the connection check module 4 placed at the drip chamber 6, the controller 30 carries out a further evaluation regarding the fluid connection between the reservoir 2 and the pump 14A. Namely, the controller 30 additionally evaluates the signal from the flow sensor 8, so that, in case the evaluation leads to the result that the signal from the flow sensor 8 indicates that there is no starting of flow of a drug through the drip chamber 6 although the pump 14A has started, the controller 30 causes the operation of the pump 14A to be immediately stopped. However, before carrying out the aforementioned evaluations, in a first step the controller 30 checks on the basis of the signal from upstream and downstream occlusion pressure sensors (not shown here) whether or not the pump 14A is completed by having its both parts, i.e. the pump cartridge 16 and the pump module 18A, being attached to each other, and only in case the signal indicates that the pump 14A is completed in that way before the start of the infusion, and just thereafter the controller 30 evaluates the signals and data from the flow sensor 8 and the label 36. The flow of the correct medication or drug from the reservoir 2 associated to the correct protocol of the pump 14A starts with activation of the motor (not shown) of the pump 14A so that a variation of the fluid rate and, thus, of the fluid connectivity is validated.

As further schematically shown in FIG. 1a, the controller 30 can be connected to the internet or a hospital intranet 31, via a cable 32 or wirelessly, and communicate via the internet or intranet 31 with an external server 33 which includes data bases like a drug and protocol library 35 so that the controller have access to the data stored in said data bases.

Moreover, as a further label a patient label can be used in which data identifying the specific patient are stored, wherein as an example in FIG. 1a such patient label is schematically illustrated as a small block and designated by the reference numeral "37". Additionally as a still further label, a so-called location label can also be used which is provided at the patient's bed or at the location or in the room where the patient's bed is situated and stores the data identifying said location or said room, wherein as an example in FIG. 1a such label is schematically illustrated as a small block and designated by the reference numeral "39". With respect thereto, in this case, the label reader 38 is adapted to also read data from the aforementioned further labels 37 and 39.

So, there is provided a safety system including the flow sensor 8, the label 36, the label reader 38 and the controller 30 as well as the detecting element 19 in the embodiment according to FIG. 1a. Moreover, in the embodiment of FIG. 1a the connection check module 4 (without the flow sensor 8 and the label reader 38), the upstream tube 10 and the pump 14A are considered to commonly define an infusion pump unit.

Alternatively, according to a modification of the embodiment of FIG. 1a there is provided no drip chamber so that the upstream tube 10 is directly fluidly connected to the outlet port of the reservoir 2. For the fluid connection, the inlet of the upstream tube 10 is provided with a spike to be put into the outlet port of the reservoir 2 wherein the connection check module 4 is attached to said spike and as fluid connection detection means there is provided an active valve instead of the flow sensor adapted to close and open the upstream tube 10 and to be controlled by the controller 30. Such a modified connection check module 4 according to a second variation is schematically illustrated in FIG. 1c which differs from the first variation shown in FIGS. 1a and b in that instead of the drip chamber 6 and the flow sensor 8 the connection check module 4 comprises an active valve 10 through which the upstream tube 10 is led. The valve 9 is adapted to close and open the upstream tube 10 and is preferably configured as a pinching valve squeezing the upstream tube 10 for closing it. For checking the fluid connection between the reservoir 2 and the pump 14A, the controller 30 activates the valve 9 to close the upstream tube 10 (in particular by squeezing it) at the start of the infusion until an upstream occlusion or a pressure near occlusion or a predetermined decreasing pressure is detected by an occlusion detector, and, if so, the controller 30 activates said valve 9 to open again so as to continue the infusion; or in case the pressure slope is flat or the volume infused reaches a limit, an alarm may indicate that the fluid connection is wrong. So, the connection check module 4 may be embodied with two variations wherein a first variation is schematically shown in FIGS. 1a and b and the second variation in FIG. 1c.

In FIGS. 2a-c, the pump cartridge 16 including the pump mechanism, in particular a rotary peristaltic pump mechanism, (not shown) is shown in greater detail. As to be seen from FIGS. 2a-c, the pump cartridge 16 is provided with a spike 40 which is attached to the inlet port 12 or alternatively itself can define the inlet port. The spike 40 is provided to be put into the outlet port (not shown) of the reservoir 2 so as to create a fluid connection between the reservoir 2 and the pump cartridge 16. Moreover, the pump cartridge 16 comprises on the one side being a front side an air vent 42 and on the other side being the rear side a coupling element 44 to be driven by the motor of the second part or pump module 18A as well as an upstream occlusion detector hole 45 and a downstream occlusion detector hole 46. The upstream occlusion detector hole 45 and the downstream occlusion detector hole 46 form together with upstream and downstream occlusion detectors (not shown) provided at the pump module 18A upstream and downstream pressure sensing means, respectively. The pump cartridge 16 of FIGS. 2a-c is to be attached with its rear side to the pump module 18A of FIG. 1a so as to create a coupling between the motor in the pump module 18A and the coupling element 44 is created, and upstream and downstream occlusion detectors are at least partly inserted into the upstream and downstream occlusion detector holes 45, 46, respectively. A pin 47 is provided at the rear side of the pump cartridge 16 and adapted to activate the detecting element 19 at the pump module 18A so as to indicate that there is used a pump cartridge 16 of the type with direct connection as shown in FIGS. 2a-c wherein the spike 40 is directly fluidly attached to the inlet port 12 of the pump cartridge 16 and provided to be directly put into the inlet port of the reservoir 2. Preferably the detecting element 19 is embodied as a switch to be pressed by said pin 47. In case of using a pump cartridge 16 of a different type wherein an upstream tube 10 is connected to its inlet port 12 according to the embodiment shown in FIG. 1a so that the spike is provided at the inlet of the upstream tube 10, there is no pin or the pin is flat so that the detecting element 19 is not activated. So, in case of the provision of the upstream tube 10 the controller 30 can give an alarm if the connection check module 4 is missing wherein the detecting element 19 at the pump module 18A is activated by the aforementioned pin at the pump cartridge 16.

FIG. 3 shows the system according to a further embodiment which differs from the embodiment of the system of FIG. 1a in that the upstream tube 10 and the connection check module 4 are missing so that the pump 14a is directly fluidly connected to the reservoir 2 by means of the spike 40 put into the outlet port of the reservoir 2 without an upstream tube therebetween. However, in order to have a convenient location for the label reader 38 close to the label 36 at the reservoir 2, the label reader 38 is included in the pump module 18 of the pump 14A, as shown in dotted lines in FIG. 3.

Since the detecting element 19 shows that there is no upstream tube and the connection check module 4 is not needed for safety in the embodiment of FIG. 3, the controller 30 can only evaluate the data read from the label 36 by the label reader 38 for validation of the drug contained in the reservoir 2. However, since the provision of a drip chamber is mandatory in some countries like the Netherlands it is also conceivable to additionally use a flow sensor like the flow sensor 8 of FIG. 1a in particular to be provided at the outlet 20 of the cartridge 16 of the pump 14A so as to also have flow rate information.

Figures 4A, 4B:
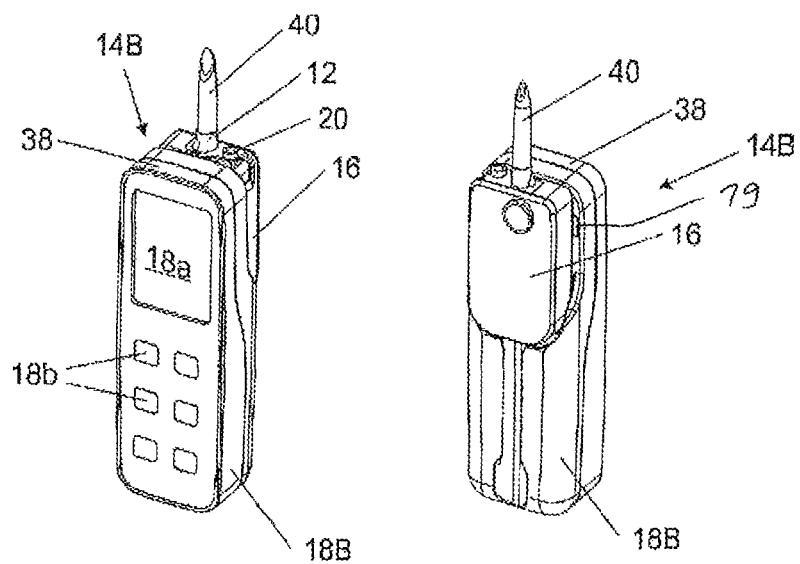
FIGS. 4a-b show a pump according to a preferred embodiment (provided as a miniature pump) in a perspective front view (a) and in a perspective rear view (b)

FIGS. 4a-b show a further preferred embodiment of the pump 14B which is embodied as a pocket sized or miniature pump. This pump 14B is adapted to accompany the same cartridge 16 as the pump 14A schematically shown in the FIGS. 1a and 3. In contrast thereto the pump module 18 is different and in particular comprises a display 18a and keys 18b for a convenient use and control. Moreover, the pump module 18 additionally includes the label reader 38 whose face, in the illustrated embodiment, lies free at the upper side of the pump module 18 at a location where the reference numeral "38" is pointing to.

Figure 5:
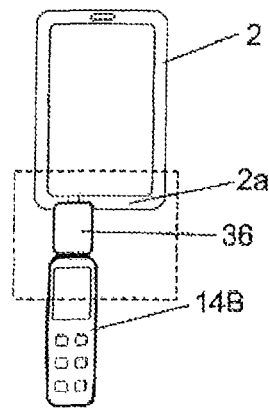
FIG. 5 shows the medication infusion system comprising the pump of FIGS. 4a-b and the medication infusion safety device according to the second embodiment.

FIG. 5 shows the system according to an embodiment which is modified over the embodiment of FIG. 3 in that instead of the pump 14A the pump 14B of FIGS. 4a-b is used. Further, the pump module 18 of the pump 14B can also be provided with the functions of the controller 30 so that in principle the controller 30 shown in FIG. 3 can be omitted; however, nevertheless it is also conceivable and advantageous to additionally provide a controller which communicates with the pump 14B and may also communicate with an external server so as to have an easier access to a drug library and other information and data relevant for the specific patient as shown in FIG. 1a (cf. reference numerals "33" and "35") and to allow an easier local programming and a multiple pump handling.

Figure 6A:
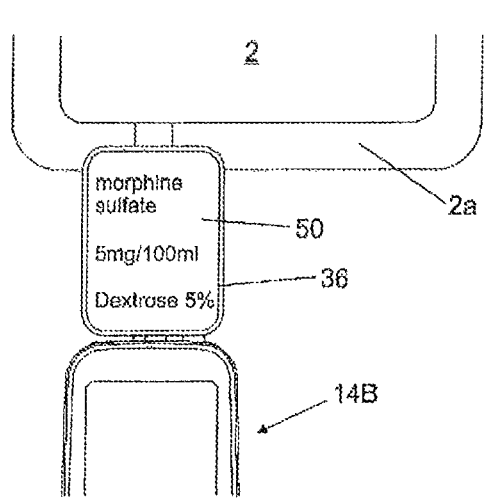
FIGS. 6a-b are an enlarged partly illustration of a portion of the system of FIG. 5, in particular showing a label in a front view (a) and a perspective rear view (b)
Figure 6B:
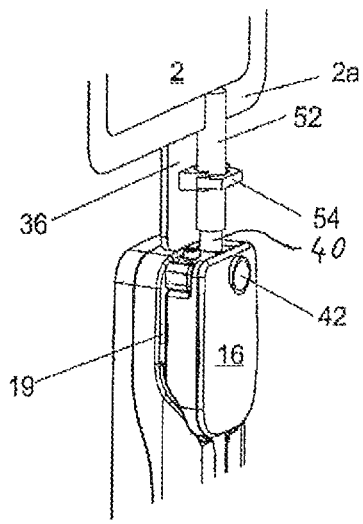

From FIGS. 6a-c the label 36 according to preferred embodiment is to be seen in an enlarged view. As shown in FIG. 6a, the label 36 comprises at its front side a display 50. Preferably the display 50 is a powerless display which in particular consists of an electronic paper element. Also preferably the label 36 includes an RFID data memory (not shown) which is electrically connected to the display 50 for both programming data and transferring power.

As to FIG. 6b, first of all it is to be noted that in this figure the already above mentioned outlet port of the reservoir 2 is completely shown and designated by the reference numeral "52". In the shown embodiment, the outlet port 52 is provided at the lower edge portion 2a of the reservoir 2 and configured as short cylindrical tube. The outlet port 52 comprises an open free end into which the spike 40 is put for a direct fluid connection of the reservoir 2 to the pump cartridge 16, as shown in FIG. 6b.

As further to be seen from FIG. 6b, the label 36 comprises a plate-like body. Further, at the rear side of the label 36 there is provided a U-shaped fixture a clamp 54 which operates as a fastening means for releasably attaching the label 36 to the outlet port 52 with the clamp 54 surrounding the outlet port 52 in a closed position. Usually, the outlet port 52 of the reservoir 2 has standard dimensions to let a spike 40 having standard dimensions to be inserted, whereas the external dimensions may be slightly different from manufacturer to manufacturer, so that the aforementioned fixture with the clamp 54 may preferably include a dimensional adapter made as somewhat like a spring or made of rubber for preventing rotation of the label 36 around the outlet port 52. Alternatively, a separate plate can be used for supporting the label. Whereas FIGS. 6a-c (as well as also FIGS. 1a, 3 and 5) show the label 36 attached to the outlet port of the reservoir 2, it is also conceivable to fasten the label 36 beside the outlet port 54 at the lower edge portion 2a of the reservoir 2 so as to protrude downwards therefrom. In such a case, the label 36 can be integral with the reservoir 2 and can preferably be embodied as a printed RFID adhesive label which is supported by an extension foil substrate (not shown) made of the material of the reservoir 2 and protruding to a level or height much lower than the level of the lower edge 2a of the reservoir 2 so that the antenna (not shown here) of the RFID label is at reading distance from the label reader 38.

Figure 7A:
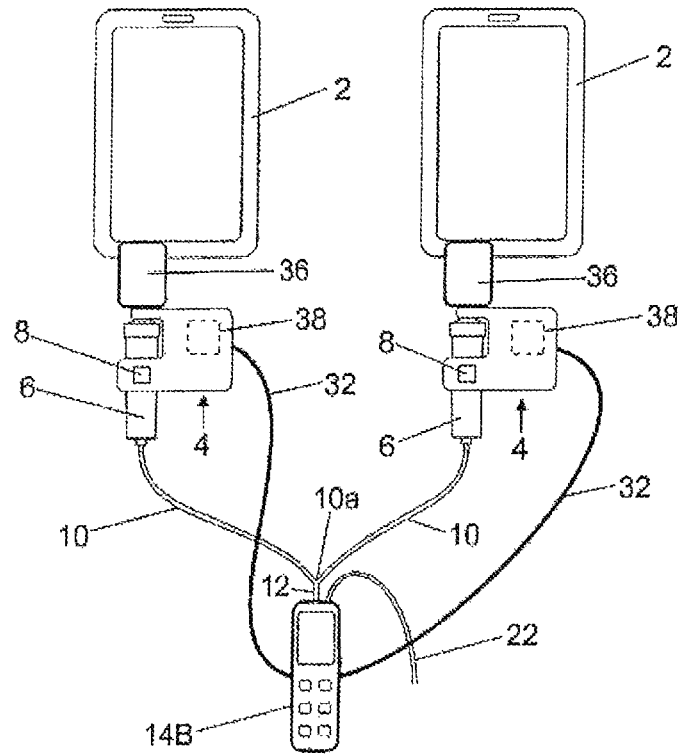
FIGS. 7a-b show a medication infusion system in a piggyback configuration comprising the pump of FIGS. 4a-b and medication infusion safety devices according to the first embodiment using a cable connection (a) and a wireless connection (b)
Figure 7B:
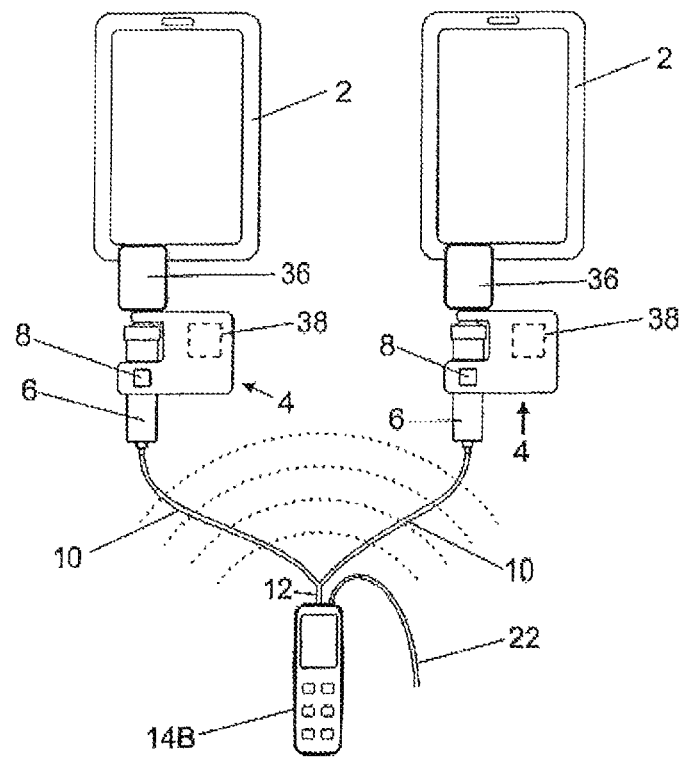

FIGS. 7a-b show a system with a piggyback setup with one pump 14B wherein each of the reservoirs 2 is fluidly connected to the pump 14B in a similar manner as shown in FIGS. 1a-c. So, each reservoir 2 is fluidly connected to the pump 14B via a drip chamber 6, a spike (not shown here), an upstream tube 10 and a Y-connector 10a to the inlet port 12 of the pump 14B. Therefore, regarding the type of connection the embodiment of the system of FIGS. 7a-b corresponds to the embodiment of the system of FIGS. 1a-c with the only difference that the miniature pump 14B of FIGS. 4a-b is used as a pump. Whereas in the embodiment of FIG. 7a the power and data connection between the connection check modules 4 and the pump 14B is realized by electrical cables 32, FIG. 7b shows an embodiment with a wireless power and data communication after pairing devices. Alternatively, the flow sensor 8 of the connection check module 4 may also be replaced by a pinching valve 9 wherein the drip chamber 6 is removed according to the second variation shown in FIG. 1c. In these two variations, the change from one reservoir 2 to another reservoir 2 results in different pump actions both having significant advantages over the prior art. In the variation with the flow sensors 8 as shown in FIGS. 7a-b, the change of the flow due to the change of the height of the reservoir 2 or the change of the level of clamping results in a change of the infusion protocol to be done automatically or to be validated by a nurse wherein anyway the old protocol is immediately stopped. In the alternative variation (not shown here) comprising active valves, the valves may be automatically alternated after a predetermined volume or time is reached by closing the one valve infusing and opening the other valve not infusing yet, so that the sequencing of medication delivery each with the associated protocol is assured since the controller knows which valve is associated to which medication. In case there is no connection with one piggyback or sequencing reservoir 2, a connection check is done during a first infusion cycle with each reservoir 2. In a piggyback configuration, the sequencing may be done with more than two reservoirs 2. Further, it is to be added here that at least most of the functions of the controller 30 shown in the FIGS. 1*a* and 3 can be implemented in the pump 14B. However, it is also conceivable to additionally provide a controller similar to the controller 30 of the FIGS. 1*a* and 3 and possibly an external server wherein the communication between the controller, the connection check modules 4, and the pump 14B as well as the external server may be wired or wireless.

Figure 8:
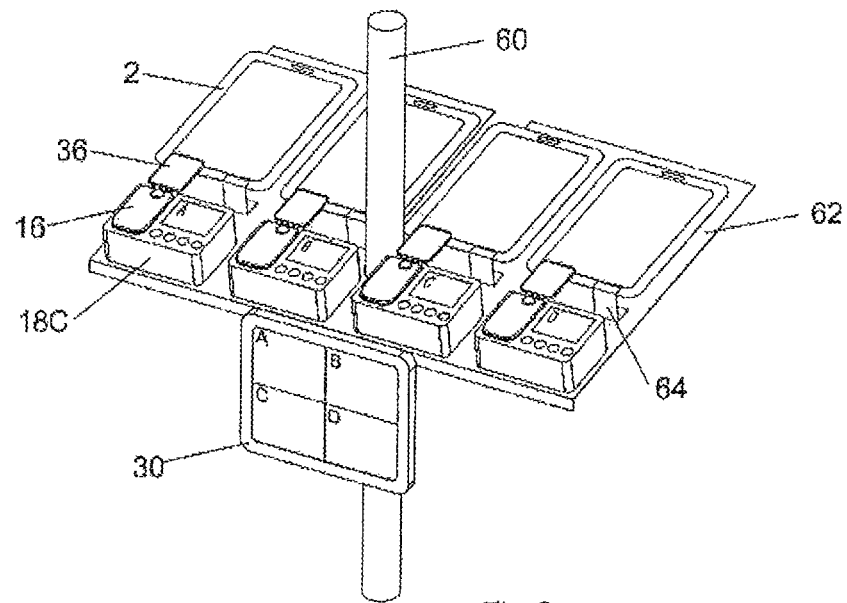
FIG. 8 is a perspective view of a medication infusion system arrangement comprising syringe pumps, medication infusion safety devices according to the second embodiment and an inclined rack in particular supporting medication reservoirs and the syringe pumps.

FIG. 8 shows a space saving syringe pump replacement arrangement comprising a vertical pole 60 to which a plate-dish or rack 62 and below the controller 30 are fastened. Syringe pumps require no upstream tubes and have a good flow constancy index (defining the linear flow per screw revolution) so that they are preferred by the personnel for certain drugs or medications having a short life. Since pump cartridges 16 as shown in FIGS. 2*a-c* have a good constancy and accuracy as syringe pumps they can replace them if lower space is needed. The rack 62 is provided as a support element for supporting a plurality of combinations of a reservoir 2 and a syringe replacement peristaltic pump 14C arranged side by side. The rack 62 is inclined so as to allow air to go up within the reservoirs 2 while there is enough friction to let the reservoirs 2 be laid upon the rack 62 without hanging, but additionally supported by stops 64. As to be seen from FIG. 8, the pump module 18C of the syringe pumps 14C is adapted to accompany the already above mentioned pump cartridge 16. Each syringe pump 14C is directly fluidly connected via its pump cartridge 16 to the reservoir 2 in the same manner as shown in the FIGS. 3 and 5 with the label 36 attached to the outlet port (not shown here) of the reservoir 2. So, regarding the direct connection, the embodiment of FIG. 8 corresponds to the embodiments of FIGS. 3 and 5 in principle. For reading the label 36 each syringe pump 14C includes an associated label reader (not shown here). As in the other embodiments, the controller 30 is provided for all complex programming and server communication and with a large viewing window.

Figure 9:
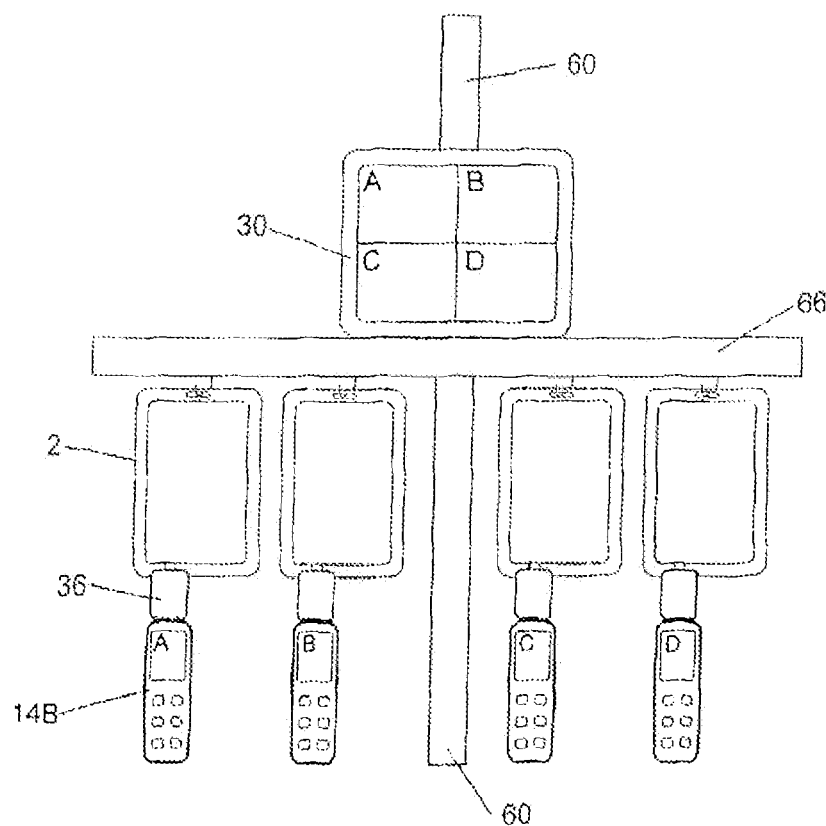
FIG. 9 is a front view of a medication infusion system comprising the pumps of FIGS. 4a-b suspended from the respective reservoirs which are attached to a horizontal bar, and further comprising medication infusion safety devices according to the second embodiment.

FIG. 9 shows an arrangement comprising a vertical pole 60 to which a horizontal bar 66 is attached wherein the controller 30 is mounted to the vertical pole 60 above the horizontal bar 66 at eye level and a plurality of reservoirs 2 are hanged from the horizontal bar 66. As further to be seen from FIG. 9, miniature pumps 14B of FIGS. 4*a-b* are used wherein each pump 14B is directly fluidly connected to the outlet port of an associated reservoir 2 wherein the pumps 14B are suspended from the reservoirs 2. So, each combination of reservoir 2 and pump 14B corresponds to the embodiment of FIG. 5, wherein this arrangement simplifies the handling and the monitoring of the infusion process as the reservoir 2 does not need to be hanged as high as it is to be driven by gravity.

Figures 10A, 10B:
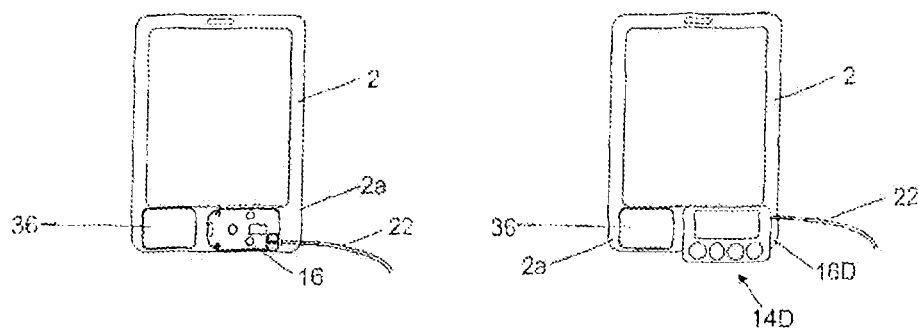
FIGS. 10a-b are a front view of a medication infusion system according to a further preferred embodiment using a medication infusion safety device according to the second embodiment without a pump module (a) and with the pump module (b)

FIGS. 10*a-b* show an embodiment wherein not only the label 36 but also the pump cartridge 16 is mounted on the lower edge portion 2*a* of the reservoir 2. Whereas from FIG. 10*a* it is to be seen only the pump cartridge 16, FIG. 10*b* shows a completed pump 14D with the pump module 18D being attached to the pump cartridge 16. For reading the label 36, the pump module 18D includes a label reader (not shown here). So, the reservoir 2, the pump module 16 and the label 36 form an integrated unit already in a state when the reservoir 2 is still empty and to be filled by a compounder or at the pharmacy or is pre-filled with a medication or drug and, hence, ready to use in a simple way as a pre-filled syringe. Accordingly, there is provided a new safe drug delivery method using the pump cartridge 16 and the label 36 which is automatically readable by a label reader integrated in the pump module 18D.

Figure 11:
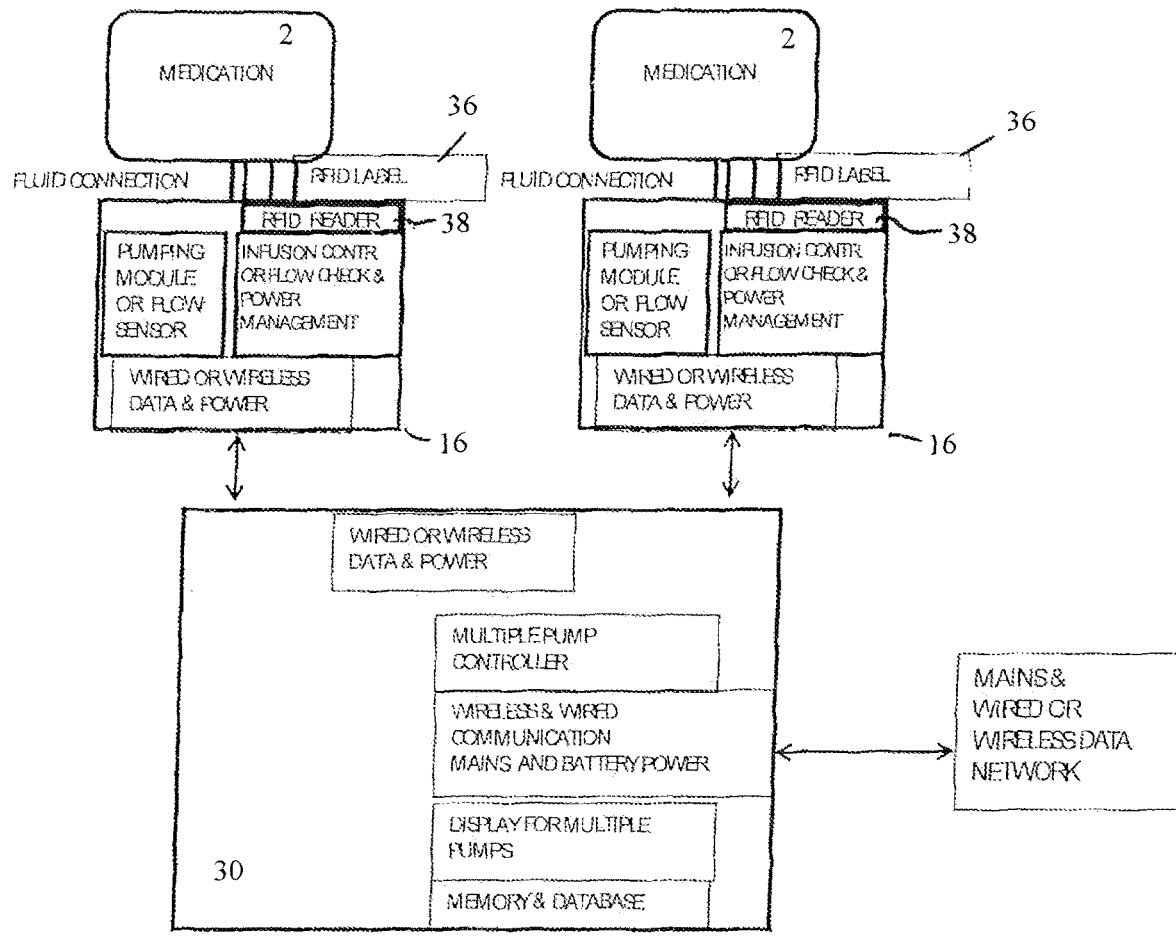
FIG. 11 is a schematic block diagram of a medication infusion system showing two infusion pump units and a controller each with functional blocks.

FIG. 11 shows a schematic block diagram of an infusion system with reservoirs 2, infusion pump units 14 and a controller 30 wherein the infusion pump units 14 and the controller 30 are illustrated with their functional blocks for a better explanation of their configuration and operation.

After all, with reference to FIGS. 4*a-b* as already explained above, a fully ambulatory bedside pump 14B with upstream and downstream occlusion measurement and air-in-line detection functions, a maximum rate of 1000 ml/h and a capability of a full fluid balance for about four days to be given with one battery change can be smaller than a cigarette packet and, thus, be easily carried in the personnels' pocket. Such a pump 14B can have a direct connection to the reservoir 2 with the absence of an upstream tube and be hanged on its spike 40 itself for a single drug infusion, or can be provided with an upstream tube 10 for a conventional infusion or a piggyback infusion as shown in FIGS. 7*a-b*. Such a preferred embodiment can comprise a simple user interface for programming, whereas all IT type functions like drug libraries and interoperability connections are stored in a multi-pump controller 30 connected by a local network (through Bluetooth low energy (BLE)) or a greater network (WiFi). Such a pump 14B can be preferably embodied as a miniature pump and can be maintained always charged by using a plate-like charger on the wall which is wirelessly charging it, or by means of the controller 30 or an IT bedside system by using a high efficient wireless power transmission such as Witricity type power technology (not shown).

Alternatively, a smaller and lighter pump can be used as shown in the FIGS. 1*a* and 3 wherein such a pump 14A includes just a driving motor and electronics as well as a very small and lightweight battery or capacitor in case of a wireless power and data connection or no battery in case of a cable connection. Wireless charging is advantageous for embodying the pump as an ambulatory pump with wireless connectivity while totally eliminating cables and resulting in a significant reduction of weight and size. For such a construction, a power supply is placed on the pump controller 30 or IT bedside system and is adapted to wirelessly charge or power all pumps or sensors on the pole with high power transmission efficiency.

As in particular shown in FIGS. 1*a-c* the flow 8 sensor contained in a combined flow detection and RFID reading module 4 preferably has an U-shape and is arranged over the drip chamber 6 spiked directly in the reservoir 2, as used by conventional pumps to infuse in drops per minute, but not provided for a connectivity validation as in the present invention. Alternatively, the flow sensor may be a Doppler flow sensor placed on the tube at the end of the spike. Also, a floating ball which is moved by the flow for opening and closing an orifice (not shown) may be used as a different kind of flow sensor.

Figure 12:
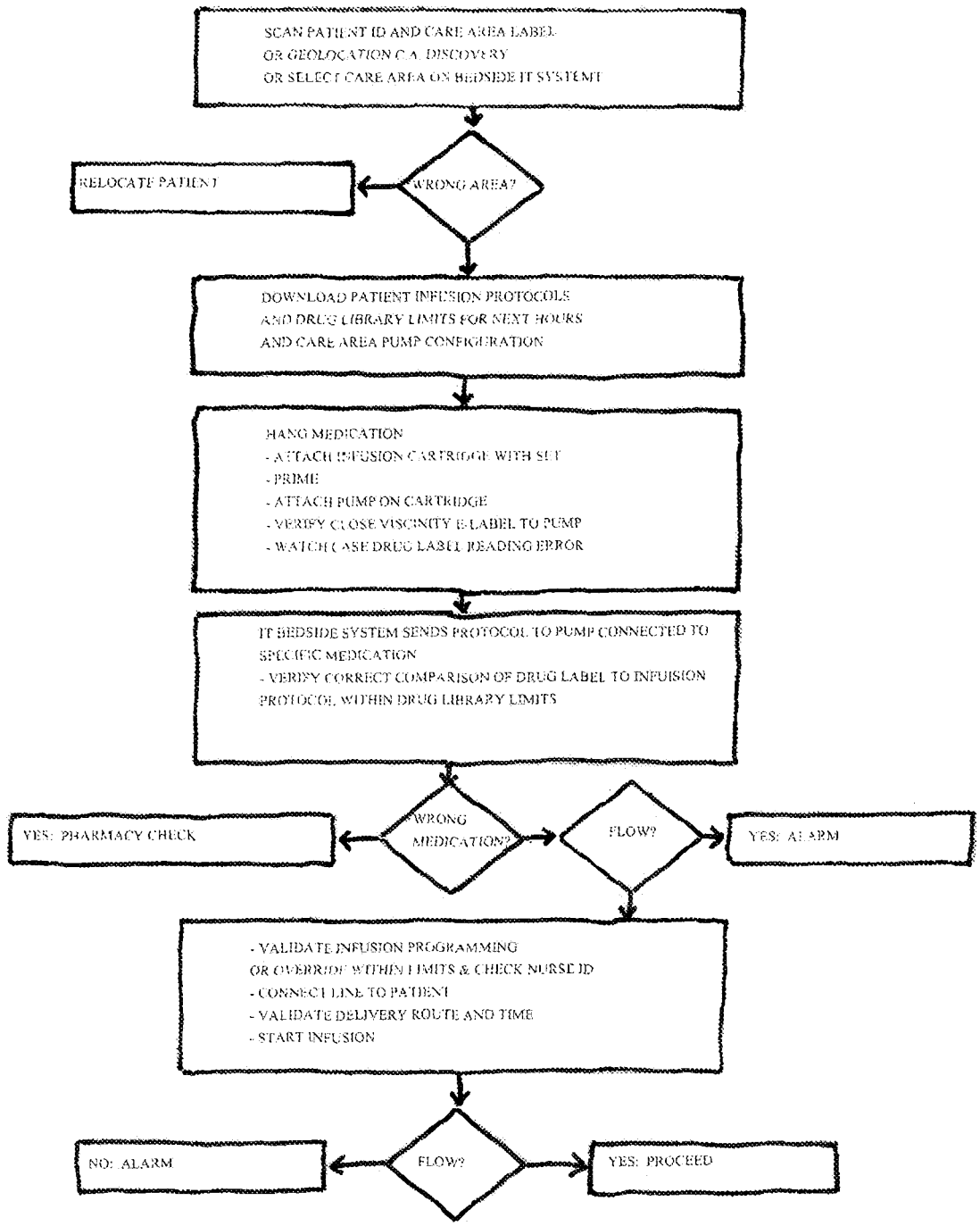
FIG. 12 schematically shows a safe infusion management procedure.

According to a preferred embodiment, two simultaneous automatic validations are achieved for the medication safety to avoid wrong drug delivery so that no human error becomes possible. The first validation is a so-called connection validation indicating from which reservoir 2 the infusion is carried out, and the second validation is a so-called medication validation indicating which medication is contained in the reservoir 2. Then, the system and the nurse in charge can double check all the "5R" rules by means of a e-prescription and electronic health record in accordance with the protocol and drug library limits for the medication which is about to be infused to the identified patient as shown in the flowchart of FIG. 12 The chart provides three identified alarms (each resulting in a termination of the process), i.e. "wrong patient location", "wrong medication not in line with the e-prescription or the medication not found in the data read from the RFID", and "wrong infusion line" (spike-reservoir connection) thus safeguarding the patient. The chart applies to both systems, i.e. direct connection or provision of an upstream tube, wherein the two last checks for flow according to the flow chart of FIG. 12 are by-passed if the detecting element 19 indicates a direct reservoir-to-pump connection. For the flow check both the aforementioned variations of the connection check module 4 with a flow sensor 8 or a pinching valve 9 can be provided by using their respective check procedures, i.e. detection of flow or detection of decreasing pressure.

In order to remedy wrong drug delivery, two preferred solutions are proposed:

1. An arrangement wherein the infusion pump unit is directly coupled with its inlet port (luer) or spike 40 to the outlet port 52 of the medication reservoir 2 without an upstream tube therebetween (cf. e.g. FIG. 6*b*), safely eliminates errors anytime due to the cooperation of the memory reading means 38 at the infusion pump unit with memory means 36 at the medication reservoir 2 only since a connection validation is obvious from the direct connection of the infusion pump unit with the medication reservoir 2.

2. A combined arrangement of a connection check module 4 including a flow sensor 8 or an active valve 9 and a memory reading means 38 safely eliminates errors anytime, in particular in case the infusion pump unit is coupled to the medication reservoir 2 via a (more or less long) upstream tube 10 whose inlet is fluidly connected to the outlet port 52 of the medication reservoir 2 and whose outlet is fluidly connected to the inlet port 12 of the infusion pump unit (cf. e.g. FIG. 1*a*), since in addition to the validation of the medication due to the reading of the memory means 36 by the memory reading means 38 (associated to an infusion protocol for this specific medication and the specific patient) a validation of the fluid connection is done by means of the flow sensor 8 or alternatively the aforementioned valve 9 whereby at the moment the infusion pump unit starts its operation and, hence, the infusion it is evaluated whether or not the flow sensor 8 detects a flow of the medication in the tube 10 going to said infusion pump unit, or in case of the provision of an active valve 9 which is to close while the pumping operation is started a decay of pressure validates the fluid connection, and, if not, the controller 30 immediately stops the operation of said infusion pump unit.

The IT bedside system may be embodied as a so-called integrated system including infusion pump units or as a so-called distributed pump system. Both embodiments are shown as functional blocks in FIG. 11 wherein the IT bedside system is connected to the memory reading means, the flow sensor or active valve and the pump in a wired or wireless manner for data (BLE or WiFi) and eventually power.

The medication safety infusion procedure is shown by the flowchart of FIG. 12 which makes evident that no human error is possible even under work pressure.

Preferably, the pump 14B of FIGS. 4*a-b* is small and handy and includes an RFID reader 38 so that the pump is able to scan the patient's ID. The patient's ID which includes an electronically readable label 37 like an ERL/RFID tag (FIG. 1*a*) and may be preferably of the same type as the label 36 (FIG. 1*a*) and embodied as a wrist ID is appropriate for downloading into the pump or the IT bedside system e-prescription data, information about the drugs and limits, infusion rates or protocols, time to infuse, delivery route, information about piggyback infusions, sequenced infusions, care area per time as intensive care unit infusions followed by ward infusions. Pump configuration data like alarm, lighting, connectivity frequency and power management preferences to be used by a hospital alarm server are downloaded when a change of the care area is verified. The provision of the drug limit from the drug library for the patient is required besides the download of the protocol in case a titration is needed. In the prior art, the aforementioned drug limit is independent from the patients, and the drug library is stand-alone for a care area. But some drugs like morphine require largely different limits from patient to patient since it is known that morphine is well tolerated by some patients so that they need more to reduce the pain, whereas the same dose might be fatal for a patient who has not used morphine so far. So, a drug library limit is provided due to an e-prescription modified by the doctor for a specific patient. This new drug library limit for any titration after the initial programming is transmitted to the infusion pump unit through network connectivity and also to the label 37, respected by the infusion pump unit after reading said label 37 and programming the infusion. So, practically a drug library in the infusion pump unit is not needed anymore. In case an e-prescription is not yet ready, the limit from the drug library for the drug can be transferred into the label 37 so that it is considered during the programming. The server based system may require a double check verification by separate care persons in the light of the e-prescription as needed in some countries so as to be ready for infusion.

The infusion protocol and the whole "5R" safety check rule are downloaded from a distant server 33 (FIG. 1*a*) for the patient cared by the system on the pole 60 (cf. e.g. FIG. 9), wherein a secondary check validation by a nurse having infusion data in written form or on a mobile device like a tablet is required. An RFID (cf. label 39 in FIG. 1*a*) at the bed or the wall can identify the care area and the room number. In case a barcode is used, the barcode can be read by a camera of a mobile device, and in case an RFID is used, the RFID can be read by an NFC reader on the same device or unit.

With the implementation of the aforementioned first solution (without upstream tube) as shown in FIG. 3, the reservoir 2 is directly fluidly connected to the infusion pump unit including an RFID reader which is coupled to an IT system controller 30 below on the pole in a wired or wireless manner, wherein in particular the following variations are conceivable:

a) The pump can be arranged at a horizontal pole bar together with the RFID reader (which can be integrated in the pump or mounted at the pole bar), the spike of the pump is put into the outlet port of the reservoir for direct fluid connection, and the height of the arrangement of the top of the reservoir is adjustable since the level of arrangement of the lower part of the reservoir and the connection is determined by the mounting of the pump at the bar.

b) There are hooks at the bar, the pump module with the RFID reader is provided at a vertical rod below, the pump module is attached to the cartridge having the spike, and a display is provided at a horizontal bar as exemplarily shown in FIG. 9.

c) According to FIG. 5 a complete pump 14B including the RFID reader 38 or according to FIG. 3 a pump 14A with the RFID reader 38 is spiked into the reservoir 2 on the top of a pole resulting in a direct reading of the medication and a wireless or cable connection to a multi-pump controller 30 which is classically placed below.

d) In case of a syringe multi-pump replacement arrangement the replacement bags being small (50 to 100 ml) do not need necessarily to be hanged, but can be arranged on an oblique or inclined plate-rack, while the spike itself at the lower end has the function of a stop together with a rib on the plate-rack, and the cartridge with the spike is fitted to the pump module with a cable connected to a multi-pump display unit, as shown in FIG. 8.

e) A cartridge 16 may be provided at a reservoir 2 which is pre-filled with medication or empty (for compounding) and is adapted to accept a pump 14D or a pump module 18D by press-fitting, wherein the label 36 is arranged at its border at a distance for reading by the RFID reader, as shown in FIGS. 10a-c.

In case of the aforementioned second solution wherein a combination of RFID reader 38 and flow sensor 8 or active valve 9 is provided as shown in FIG. 1a-c, in particular not only the data of the medication are read from the RFID 36 but also a signal from the flow sensor 8 is considered for the recognition of a correct reservoir-pump connection, or according to the actuation of the valve 9 at the start of infusion the pressure is detected, wherein the RFID 36 and the flow sensor 8 or active valve are provided at the same reservoir 2 or at least associated to the same reservoir 2. In case of the start of an infusion or sudden change of the reservoir it is for safety reasons important to validate both the drug in the reservoir to check if the protocol as well as the reservoir-pump connection and, hence, the drug-pump connection is correct.

In a classical configuration with reservoirs hanged on the top of a pole and a multi-pump system provided at the pole, infusion lines or tubes pass through the pumps to the collector, and flow controllers integrated with RFID readers are connected to a pump through cables for safe infusions. In this case, of course the cables can be alternatively provided on the top of the pole where the reservoirs are suspended from, or there are no cables but wireless power and data connectivity.

In a piggyback infusion configuration two reservoirs are used which are connected upstream to the pump, wherein the infusion is carried out by one pump from the one or the other reservoir depending on their height and, thus, the hydrostatic pressure of the medication. Medication errors which often occur in such a configuration are described by the following sentence quoted from Idataresearch Infusion Pump Market Survey 2015: "However, unit sales for secondary intravenous sets are growing significantly slower than sales of primary intravenous sets as a result of safety concerns regarding the occurrence of medication error".

According to the preferred embodiment as shown in FIGS. 7a-b, there is provided an Y-connector 10a collecting the medication fluids from the two upstream tubes 10 each fluidly connected to a reservoir 2 while the provision of a clamp (not shown) for clamping only one reservoir or the adjustment in different heights may be used to switch between reservoirs as it is the today's practice. In such a case, two connection check modules 4 each comprising a flow sensor 8 or active valve 9 and an RFID or ERL/RFID reader 38 have to be provided on each reservoir for safety reasons. The programming defines a protocol for each medication so that the rate switching can be automatic since after the change of the clamping of an upstream tube or the change of the height of a reservoir 2 the pump knows from the flow sensor which medication is infused, or itself activates the one valve after deactivating the other valve for finishing the infusion according to a sequence program. The latter procedure is particularly useful in case of the provision of a multiple medication sequence as in chemotherapy protocols wherein the infusion of as many as eight medications one after the other is done. A safety check protocol as described above which uses in case of the provision of flow sensors a flow sensing at the start of infusion or in case of the provision of a valve a pressure decay sensing (with the valve closed) at the start of infusion, is mandatory for each reservoir 2 resulting in an elimination of a foreign spike insertion risk. Of course, in a connection check module may have both a passive flow sensor and an active valve to be able to do sequencing while evaluating the flow rate and to allow the user to act on the reservoirs 2 to alternate infusion instead of acting on the infusion pump unit or to let it done automatically. The active valve may be of bistable type for low power (powered on commutation only) as known in watering applications in the prior art.

In FIG. 7b a similar configuration is shown but wherein the flow sensor 8 and the ERL/RFID reader 38 are provided for wireless connection so as to wirelessly transmit power by means of a high efficient wireless power transmission as known in the prior art and data (in particular through a Bluetooth low energy (BLE) transponder or WiFi). The modules 4 may be hanged on a hook (not shown) for the reservoirs 2 at the pole when not in use so they are not lost.

Another simple safety solution is that the pump reads the RFID label 36 of each of the two reservoirs at a first stage, then the protocol for the medication from each reservoir is defined (on the basis of an e-prescription or locally programmed), and the switching between the medications is done by height difference, while the lower medication reservoir is located just close to the top of the pump so that the RFID reader in said pump constantly reads the RFID label 36 at said reservoir. After switching, the pump operates by a default protocol of the medication which is not identified by a label or tag since the medication now comes from the higher (non-readable) reservoir. Such an implementation without fluid connection check does not fully guarantee the prevention of a medication error, but due to its simplicity the prior art practice may be replaced since it has been even less safe.

Conventionally, medication reservoirs for infusion are hanged on the top of a pole since infusion by gravity is the most common medication delivery method wherein a certain height is needed to build a minimum pressure in the infusion line, and all nurses are familiar with such a practice. When using pumps, there is no reason to have reservoirs on the top of the pole since they build pressure by default.

For a preferred implementation of the present invention, the reservoirs are re-arranged so that a pump at nurse sight or bed level may be directly connected to an assigned reservoir, without the provision of an upstream tube, according to the safety rules of the present invention, which preferably requires the readable label 36 at the reservoir 2 to be in close vicinity to the label reader 38 at or in the pump.

In FIG. 8 the inclined plate 62 is shown which support a plurality of reservoirs 2 side by side so that air contained in the reservoirs 2 can still go up, but on the plate 62 there is enough friction to hold the reservoirs 2 in place without hanging, wherein pump modules 18C and, hence, the pumps 14C themselves aligned in a horizontal row also form somewhat like a natural stop for the lower end of the reservoirs 2 which, thus, are prevented to fall down to the floor. The IT controller 30 or bedside system controls all the pumps and have all necessary IT functions. Such a configuration is most needed in a multiple syringe pump replacement arrangement, where reservoirs are small with a maximum volume of 100 ml and 8 reservoirs and pumps are positioned in a row, which takes as much space as one single syringe pump configuration in the prior art, which full safety and readability of the medication and the protocol per infusion line.

There may be another arrangement of reservoirs in a vertical orientation wherein the pumps and displays are arranged on the bottom, but since they are vertical they need to be hanged from individual rods having a hook adjustable in height.

In FIG. 9 there is shown another arrangement of the reservoirs 2 hanged below the bar 66, wherein the pumps 14B are positioned at their bottom wherein each reservoir 2 comprises a display at its top, whereby the setup and the infusion verification are simplified.

In the prior art, there are electronic labels e.g. found in supermarkets which includes an electronic paper 8-segment display for showing the prize of a product without the provision of a battery, since such paper displays once programmed (in particular through an RFID powering and communicating device) they retain for a long time the data input by programming without further need for power. According to a preferred embodiment, an alphanumeric or graphical electronic paper display 50 (FIG. 6a) is used in cooperation with an RFID tag reader/writer which is preferably provided on a mobile device or implemented in a personal computer and transmits data and power to the RFID tag during programming. So, in this embodiment, data are saved in a non-volatile memory and also transmitted to a driver of the electronic paper display so that they are displayed immediately in order to have a visualization without any more power until a new programming, whereas the RFID tag sends stored data to an RFID reader anytime when powered and tagged by it. Preferably, the RFID tag or label 36 comprises an attachment or fitting element 54, in particular formed like a U with a clip fastener closing a loop for fastening at the outlet port 52 of the medication reservoir 2 which port is provided for spike fluid connection and is usually embodied as a short tube protruding from the reservoir 2 (cf. FIG. 6b) wherein it is held from the back side and comprises the display 50 at the front side. The label or tag includes electronics in between and in the bottom portion the RFID tag at a close reading distance to the label reader at or in the pump. Such a label is light weight and practically adds almost no weight to the medication reservoir to which it is attached. The label 36 including the display 50 is made for multiple use after infusion and return to the pharmacy so as to reduce paperwork and the risk of a hand-written label misreading and, hence, to ensure medication safety. It is watertight and made to be easily disinfected for multiple uses.

This label and associated NFC programmers implemented as mobile applications or to be connected via USB can make automation and safety according to the present invention in an easy way and without the need of high infrastructure expenses. A USB programmer can appear as a normal printer in the personal computer operating system by using an adequate driver so that the transfer of e-prescription or full "5R" data to the smart label is simple. The label may display less information than stored in its memory and transmitted by the RFID reading process. The transfer of most infusion information in this way enables the use in less networked hospitals, nursing homes or home care. For safety and documentation reasons, a smart label may also have a programming history record, and a write protection may be achieved by a code written into the label or tag and needed to be known by the programmer with the next programming to allow rewrite.

It is a novel way to prepare a smart label for medication validation for relatively short storage or to complete the labeling of a pre-filled medication reservoir after adding more medication so that its final labeling is to be changed under avoidance of errors. Such an e-labeling-tag device may be programmed with medication data in the course of preparation of a compounded medication in the pharmacy of a hospital, by a home care provider or by a nurse service, wherein said data in particular include a drug name, concentration, diluter, and possibly the patient's name and room number, as well as delivery route, time to infuse, infusion protocol and its limits for the patient's care area. The programming can be done by means of a mobile device equipped with an NFC programming function or by means of a PC with a tag programmer. Also an application can be used which includes the drug names library and provides the function for predicting and proposing missing letters while writing on a touchscreen or keyboard so as to simplify the writing process in case of inputting a prescription from paper. An e-prescription is downloaded wirelessly or by wire communication to the application by using interoperability standard protocols and transferred to the tag device for intermediate displaying the contents of the prepared reservoir, to be reviewed by the pharmacist. So, according to a preferred embodiment the label or tag reader provided at the infusion pump unit or in the connection check module including a flow sensor or an active valve is allowed to read the contents of the medication reservoir at start and during infusion.

The display 50 of the label 36 (cf. FIG. 6a) may optionally be in color and comprises a function for highlighting the information of the drug, therapy and/or location by a certain color so as to further avoid use errors. The label may also comprise a button with piezoelectric press-to-power means. If needed, all memory data pages are shown on the display consecutively by pressing said button so as to come back after some time to show the drug name or the patient's name and room number preferably to be displayed before the infusion, and the drug name preferably after being powered by the reader when a pump spike has been attached to the outlet port of the medication reservoir. Moreover, a similar page scroll may be done in case of tagging the tag by means of a reader which powers it. Technically, the electronics of the tag may be all hardware including a driver and designed by means of VHDL hardware descriptive language for a high volume application or microprocessor based for lower volume application. As known in the art, RFID tags or labels comprise a capacitor to be charged so as to store enough power needed in particular for the display, the EEPROM or flash memory storage and wireless RFID data communication. Electronic paper displays as known in the art draw no power after being written and have a good readability without the need of any backlight.

The invention claimed is:

1. A medication infusion safety device, comprising:
a medication reservoir containing a medication;
an infusion pump containing a first part which includes a pump mechanism and is provided with a spike adapted to insert into at least one outlet port of the medication reservoir and a second part containing a motor for driving the pump mechanism of the first part; and
a memory reader associated with the second part of the infusion pump and adapted to read data when the infusion pump is coupled to the medication reservoir,
wherein the infusion pump is coupled to the medication reservoir with a distance between a memory and the memory reader being equal to or lower than a predetermined maximum reading distance of the memory reader, wherein the predetermined maximum reading distance is determined to be less than a maximum reading distance;
wherein the second part of the infusion pump is adapted to control an infusion based on an evaluation of data read by the memory reader so that only when the evaluation determines that the medication is correct, the infusion from the medication reservoir is initiated.

2. The medication infusion safety device of claim 1, further comprising a memory adapted to be associated with the medication reservoir and to store data identifying the medication.

3. The medication infusion safety device of claim 1, wherein the second part of the infusion pump comprises control keys for controlling operation of the infusion pump.

4. The medication infusion safety device of claim 1, wherein the memory reader is adapted to read the data from the memory through a direct wireless connection.

5. The medication infusion safety device of claim 1, wherein at least a portion of the first part of the infusion pump is inserted into a portion of the second part of the infusion pump.

6. The medication infusion safety device of claim 1, wherein the infusion from the medication reservoir is initiated only when the evaluation determines that the medication is correct.

7. The medication infusion safety device of claim 1, further comprising a flow sensor to detect a rate of flow from the medication reservoir to the infusion pump.

8. The medication infusion safety device of claim 7, wherein the infusion pump is configured to receive a signal from the flow sensor and control an operation of the infusion pump based on the signal from the flow sensor.

9. The medication infusion safety device of claim 7, further comprising a controller, wherein the controller is configured to receive a signal from the flow sensor and control an operation of the infusion pump based on the signal from the flow sensor.

10. The medication infusion safety device of claim 9, wherein the controller comprises an input screen configured to receive an input.

11. The medication infusion safety device of claim 1, wherein the at least one outlet port is a circular tube that comprises an open free end to receive the spike.

12. The medication infusion safety device of claim 1, wherein the spike is further adapted to insert into a second medication reservoir comprising a medication different than the medication in the medication reservoir.

13. A medication infusion safety device, comprising:
a machine-readable label associated with a medication reservoir containing a medication and configured to store data identifying the medication;
a label-reader associated with an infusion pump and configured to read data from the machine-readable label;
the infusion pump comprising a first part which includes a pump mechanism and is provided with a spike adapted to insert into at least one outlet port of the medication reservoir and a second part comprising a motor for driving the pump mechanism of the first part, wherein the infusion pump is coupled to the medication reservoir with a distance between a memory and a memory reader being equal to or lower than a predetermined maximum reading distance of the memory reader, wherein the predetermined maximum reading distance is determined to be less than a maximum reading distance;
an electronic controller adapted to control infusion in accordance with an evaluation of data read by the label-reader so that only when the evaluation determines that the medication is correct, the infusion from the medication reservoir is initiated; and
a fluid connection detector configured to detect a flow of medication through the infusion pump and to transmit to the electronic controller a signal indicating whether or not a medication from the medication reservoir is flowing through the infusion pump, the fluid connection detector configured to be provided at an outlet port of the medication reservoir and comprising a flow sensor, wherein the electronic controller is configured to control the infusion additionally in accordance with an evaluation of the signal from the fluid connection detector such that, in case the evaluation of the signal from the fluid connection detector indicates that the medication flowing through the infusion pump is not medication from the medication reservoir but medication from a different medication reservoir that is simultaneously connected to the infusion pump, the electronic controller causes operation of the infusion pump not to be started or, if already started, to be stopped.

14. The medication infusion safety device of claim 13, wherein the electronic controller causes the infusion from the medication reservoir to be started only if the evaluation indicates that the medication is a desired medication.

15. The medication infusion safety device of claim 13, wherein the second part of the infusion pump comprises control keys for controlling operation of the infusion pump.

16. The medication infusion safety device of claim 13, wherein at least a portion of the first part of the infusion pump is inserted into a portion of the second part of the infusion pump.

17. The medication infusion safety device of claim 13, wherein the medication infusion safety device is a handheld device.

18. The medication infusion safety device of claim 13, further comprising a flow sensor to detect a rate of flow from the medication reservoir to the infusion pump.

19. The medication infusion safety device of claim 13, wherein the spike is further adapted to insert into a second medication reservoir comprising a medication different than the medication in the medication reservoir.

* * * * *